US008299016B2

(12) United States Patent
Suciu-Foca et al.

(10) Patent No.: US 8,299,016 B2
(45) Date of Patent: Oct. 30, 2012

(54) ILT3 POLYPEPTIDES AND USES THEREOF

(75) Inventors: Nicole Suciu-Foca, New York, NY (US); George Vlad, Forest Hill, NY (US); Raffaello Cortesini, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 601 days.

(21) Appl. No.: 12/419,824

(22) Filed: Apr. 7, 2009

(65) Prior Publication Data

US 2009/0274685 A1  Nov. 5, 2009

Related U.S. Application Data

(63) Continuation-in-part of application No. 11/661,877, filed as application No. PCT/US2005/031380 on Sep. 1, 2005.

(60) Provisional application No. 60/622,165, filed on Oct. 26, 2004, provisional application No. 60/607,095, filed on Sep. 3, 2004.

(51) Int. Cl.
*A61K 38/00* (2006.01)
(52) U.S. Cl. ...................................................... 514/1.1
(58) Field of Classification Search .................... None
See application file for complete search history.

(56) References Cited

U.S. PATENT DOCUMENTS

| | | | |
|---|---|---|---|
| 4,515,895 A | 5/1985 | Kung et al. | |
| 4,652,447 A | 3/1987 | Kung et al. | |
| 4,658,020 A | 4/1987 | Kung et al. | |
| 4,677,056 A | 6/1987 | Dupont et al. | |
| 4,816,404 A | 3/1989 | Suciu-Foca et al. | |
| 4,818,689 A | 4/1989 | Suciu-Foca et al. | |
| 5,156,951 A | 10/1992 | Bach et al. | |
| 6,384,203 B1 | 5/2002 | Anderson et al. | |
| 6,759,239 B2 | 7/2004 | Suciu-Foca et al. | |
| 7,144,728 B1 | 12/2006 | Suciu-Foca et al. | |
| 2003/0017143 A1* | 1/2003 | Suciu-Foca et al. | 424/93.21 |
| 2003/0118997 A1 | 6/2003 | Bejanin et al. | |
| 2003/0165875 A1 | 9/2003 | Colonna et al. | |
| 2004/0241167 A1 | 12/2004 | Suciu-Foca et al. | |
| 2008/0311073 A1 | 12/2008 | Suciu-Foca et al. | |
| 2009/0202544 A1 | 8/2009 | Suciu-Foca et al. | |

FOREIGN PATENT DOCUMENTS

| | | |
|---|---|---|
| WO | WO 98/48017 | 10/1998 |
| WO | WO 00/68383 | 11/2000 |

OTHER PUBLICATIONS

Gillespie, CMAJ, 2006, vol. 175: 165-170.*
Bisikirska et al., 2005, J. Clin. Invest. vol. 115: 2904-2913.*
Banchereau et al., "Immunbiology of dendritic cells," *Annu. Rev. Immunol.*, 18:767-811 (2000).
Beinhauer et al., "Interleukin 10 regulates cell surface and soluble LIR-2 (CD885d) expression on dendritic cells resulting in T cell hyporesponsiveness in vitro," *Eur. J. Immunol.* 34:74-80 (2004).
Cella et al., "A novel inhibitory receptor (ILT3) expressed on monocytes, macrophages, and dendritic cells involved in antigen processing," *J. Exp. Med.*, 185:1743-1751 (1997).
Chang et al., "Tolerization of dendritic cells by Ts cells: the crucial role of inhibitory receptors ILT3 and ILT4," *Nature Immunology*, 3:237-243 (2002).
Ciubotariu et al., "Detection of T suppressor cells in patients with organ allografts," *Hum. Immunol.*, 62:15-20 (2001).
Ciubotariu et al., "Persistent allopeptide reactivity and epitope spreading in chronic rejection of organ allografts," *J. Clin. Invest.*, 101:398-405 (1998).
Ciubotariu et al., "Specific suppression of human CD4+ Th cell responses to pig MHC antigens by CD8+ CD28 regulatory T cells," *J. Immunol.*, 161:5193-5202 (1998).
Colonna et al., "A family of inhibitory and activating Ig-like receptors that modulate function of lymphoid and myeloid cells," *Semin. Immunol.*, 12:121-127 (2000).
Colonna et al., "A novel family of Ig-like receptors for HLA class I molecules that modulate function of lymphoid and myeloid cells," *J. Leukoc. Biol.*, 66:375-381 (1999).
Colonna et al., "Cutting edge: human myelomonocytic cells express an inhibitory receptor for classical and nonclassical MHC class I molecules," *J. Immunol.*, 160:3096-3100 (1998).
Colovai et al., "Induction of xenoreactive CD4+ T-cell anergy by suppressor CD8+ CD28− T cells," *Transplantation*, 69:1304-1310 (2000).
Cotner et al., "Simultaneous flow cytometric analysis of human T cell activation antigen expression and DNA content," *J. Exp. Med.*, 157:461-472 (1983).
Damle et al., "Alloantigen-specific cytotoxic and suppressor T lymphocytes are derived from phenotypically distinct precursors," *J. Immunol.*, 131:2296-2300 (1983).
Dhodapkar et al., "Antigen-specific inhibition of effector T cell function in humans after injection of immature dendritic cells," *J. Exp. Med.*, 93:233-238 (2001).
Garcia-Alonso et al., "CD28 expression on peripheral blood T lymphocytes after orthotopic liver transplant: upregulation in acute rejection," *Hum. Immunol.*, 53:64-72 (1997).
Groux et al., "A CD4+ T-cell subset inhibits antigen-specific T-cell responses and prevents colitis," *Nature*, 89:737-742 (1997). Haars et al., "Modulation of T-cell antigen receptor on lymphocyte membrane," *Immunogenetics*, 20:397-405 (1984).
Jenkins et al., "Antigen presentation by chemically modified splenocytes induces antigen-specific T cell unresponsiveness in vitro and in vivo," *J. Exp. Med.*, 165:302-319 (1987).
Jiang et al., "Induction of MHC-class I restricted human suppressor T cells by peptide priming in vitro," *Hum. Immunol.*, 59:690-699 (1998).
Jonuleit et al., "Identification and functional characterization of human CD4(+)CD25(+) T cells with regulatory properties isolated from peripheral blood," *J. Exp. Med.*, 193:1285-1294 (2001).
Jonuleit et al., "Induction of interleukin 10-producing, nonproliferating CD4(+) T cells with regulatory properties by repetitive stimulation with allogeneic immature human dendritic, cells," *J. Exp. Med.*, 192:1213-1222 (2000).

(Continued)

*Primary Examiner* — Amy Juedes
(74) *Attorney, Agent, or Firm* — Evans & Molinelli PLLC; Judith A. Evans

(57) ABSTRACT

This invention provides a method for inhibiting the rejection of transplanted islet cells, comprising administering to the subject a polypeptide comprising all or a portion of the extracellular domain of ILT3, wherein the polypeptide is water soluble. This invention further provides a method of treating diabetes, by inhibiting the rejection of transplanted islet cells through the administration of the polypeptide to the subject.

10 Claims, 32 Drawing Sheets

OTHER PUBLICATIONS

Kim-Schulze et al., "Recombinant Ig-Like Transcript 3-Fc Modulates T Cell Responses via Induction of Th Anergy and Differentiation of CD8+ T Suppressor Cells," *J. Immunol.*, 176:2790-2798 (2006).

Lanzavecchia, "Immunology. License to kill," *Nature*, 393:413-414 (1998).

Lechler et al., "Dendritic cells in transplantation—friend or foe?," *Immunity*, 14;357-368 (2001).

Leukocyte Immunoglobulin-like Receptor, Subfamily B. Member 4; LILRB4, OMIM 604821 (2000).

Li et al., "T suppressor lymphocytes inhibit NFKB-mediated transcription of CD86 gene in APC," *J. Immunol.*, 163:6386-6392 (1999).

Liu et al., "Inhibition of CD40 signaling pathway in antigen presenting cells by T suppressor cells," *Hum. Immunol.*, 60:568-574 (1999).

Liu et al., "Specific suppression of T helper alloreactivity by allo-MHC class I-restricted CD8+ CD28− T cells," *Int. Immunol.*, 10;775-783 (1998).

Lutz et al., "Immature dendritic cells generated with low doses of GM-CSF in the absence of IL-4 are maturation resistant and prolong allograft survival in vivo," *Eur. J. Immunol.*, 30:1813-1822 (2000).

Manavalan et al., "High expression of ILT3 and ILT4 is a general feature of tolerogenic dendritic cells," *Transplant Immunology*, 11:245-258 (2003).

Mingari et al., "Human CD8+ T lymphocyte subsets that express HLA class I-specific inhibitory receptors represent oligoclonally or monoclonally expanded cell populations," *PNAS*, 93:12433-12438 (1996).

Mingari et al., "Regulation of KIR expression in human T cells: A safety mechanism that may impair protective T-cell responses," *Immunol. Today*, 19:153-157 (1998).

Ravetch et al., "Immune inhibitory receptors," *Science*, 290:84-88 (2000).

Rea et al., "Glucocorticoids transform CD40-triggering of dendritic cells into an alternative activation pathway resulting in antigen-presenting cells that secrete IL-10," *Blood*, 95:3162-3167 (2000).

Roncarolo et al., "Differentiation of T regulatory cells by immature dendritic cells," *J. Exp. Med.*, 193:F5-F9 (2001).

Sakaguchi, "Regulatory T cells: Key controllers of immunologic self-tolerance," *Cell*, 101, 455-458 (2000).

Schwartz, "Models of T cell anergy: is there a common molecular mechanism?" *J. Exp. Med.*, 184:1-8 (1996).

Shevach, "Regulatory T cells in autoimmunity," *Annu. Rev. Immunol.*, 18:423-449 (2000).

Steinman et al., "The induction of tolerance by dendritic cells that have captured apoptotic cells," *J. Exp. Med.*, 191:411-416 (2000).

Steinman, "The dendritic cell system and its role in immunogenicity," *Annu. Rev. Immunol.*, 9:271-296 (1991).

Suciu-Foca Cortesini et al., "A late-differentiation antigen associated with the helper inducer function of human T cells," *Nature*, 318:465-467 (1985).

Suciu-Foca Cortesini et al., "Distinct mRNA microarray profiles of tolerogenic dendritic cells," *Hum. Immunol.*,62:1065-1072 (2001).

Suciu-Foca Cortesini et al., "Idiotypic network regulations of the immune response to HLA," *Transplantation Proceedings*, 17(1):716-719 (1985).

Suciu-Foca et al., "Central role of ILT3 in the T suppressor cell cascade," *Cellular Immunology*, 248:59-67 (2007).

Suciu-Foca et al., "Soluble Ig-like transcript 3 inhibits tumor allograft rejection in humanized SCID Mice and T cell responses in cancer patient," *J. Immunol.*, 178:7432-7441 (2007).

Takahashi et al., "Immunologic self-tolerance maintained by CD25+ CD4+ regulatory T cells constitutively expressing cytotoxic T lymphocyte-associated antigen 4," *J. Exp. Med.*, 192:303-310 (2000).

Balasa et al., "CD40 ligand-CD40 interactions are necessary for the initiation of insulitis and diabetes in nonobese diabetic mice," *J. Immunol.*, 159:4620-4627 (1997).

Davalli et al., "Vulnerability of islets in the immediate post-transplantation period: Dynamic changes in structure and function," *Diabetes*, 45:1161-1167 (1996).

Gregori et al., "An anti-CD45RO/RB monoclonal antibody modulates T cell responses via induction of apoptosis and generation of regulatory T cells," *J. Exp. Med.*, 201:1293-1305 (2005).

Hoffmann-Fezer et al., "Immunohistology and immunocytology of human T-cell chimerism and graft-versus-host disease in SCID mice," *Blood*, 81:3440-3448 (1993).

Klein et al., "A functional CD40 receptor is expressed in pancreatic beta cells," *Diabetologia*, 48:268-276 (2005).

Phillips et al., "Blockade of CD40-mediated signaling is sufficient for inducing islet but not skin transplantation tolerance," *J. Immunol.*, 170:3015-3023 (2003).

Vlad et al., "License to heal: bidirectional interaction of antigen-specific regulatory T cells and tolerogenic APC," *J. Immunol.*, 174:5907-5914 (2005).

Expert Opinion Ther. Patents, "CD47-Fc fusion proteins as putative immunotherapeutic agents for the treatment of immunological and inflammatory diseases," 18:555-561 (2008).

Wang et al., "A single amino acid determines lysophospholipid specificity of the S1P1 (EDG1) and LPA1 (EDG2) phospholipid growth factor receptors," The Journal of Biological Chemistry, 276:49213-49220 (2001).

Whisstock et al., "Prediction of protein function from protein sequence and structure," Quarterly Review of Biophysics, 36:307-340 (2003).

Zotova et al., "Inflammation in Alzheimer's disease: relevance to pathogenesis and therapy," Alzheimer's Research & Therapy, 2:1-9 (2010).

\* cited by examiner 1. untreated
2. HLA-DR Ab
3. HLA-DR + crosslinking Ab
4. HLA-DR + ILT3 + crosslinking Ab

ILT3 POLYPEPTIDES AND USES THEREOF

CROSS-REFERENCE TO RELATED APPLICATIONS

This application is a continuation-in-part of U.S. application Ser. No. 11/661,877, filed Mar. 2, 2007, which is United States National Stage Application of PCT Application PCT/US05/31380, filed Sep. 1, 2005, which in turn claims benefit from Provisional Application Nos. 60/622,165 filed Oct. 26, 2004 and 60/607,095, filed Sep. 3, 2004, the disclosures of all applications are hereby incorporated in their entirety herein.

Throughout this application, various documents are referenced. Full citations for these documents are presented immediately before the claims. Disclosures of these documents in their entireties are hereby incorporated by reference into this application.

STATEMENT OF GOVERNMENT INTEREST

This invention was made with government support under Contract Nos. AI2521-18 and AI55234-02 awarded by the National Institutes of Health. The government has certain rights in the invention.

BACKGROUND OF THE INVENTION

LIRs

Leukocyte Ig-like receptors ("LIRs") are a family of immunoreceptors expressed predominantly on monocytes and B cells and at lower levels on dendritic cells and natural killer ("NK") cells. Activation of various immune cell types can be prevented by negative signaling receptors through interactions with specific ligands, such as MHC class I molecules by NK cells. All of the LIR inhibitory receptors, members of subfamily B, contain a cytoplasmic immunoreceptor tyrosine-based inhibitory motif ("ITIM"). Upon MHC class I (or other ligand) engagement and tyrosine phosphorylation of the ITIM, intracellular protein-tyrosine phosphatases such as SHP1 are recruited, and an inhibitory signal cascade ensues. Other LIR receptors, members of subfamily A, with short cytoplasmic regions containing no ITIMs and with transmembrane regions containing a charged arginine residue, may initiate stimulatory cascades. One member of subfamily A lacks a transmembrane region and is presumed to be a soluble receptor (1). LIR-5, one type of LIR, is also known as immunoglobulin-like transcript 3 (ILT3).

ILT3 Fusion Proteins

A soluble fusion protein made of a soluble portion of ILT3 and the Fc portion of IgG1 is known. However, this fusion protein was used merely as a negative control in an endotoxemia study, and its potential use as a therapeutic was not disclosed (2).

Soluble ILT4

LIR-2, also known as ILT4, is an inhibitory receptor. However, its soluble form was shown to completely restore the proliferation of T-cells activated with LPS and IL-10-treated dendritic cells (3).

SUMMARY OF THE INVENTION

This invention provides a method for treating islet cell transplant rejection in a subject who has received said transplant, comprising administering to the subject a therapeutically effective amount of a first polypeptide comprising all or a portion of the extracellular domain of ILT3, wherein the polypeptide is water-soluble and does not comprise a Fc portion of an immunoglobulin, or a second polypeptide comprising (i) all or a portion of the extracellular domain of ILT3 operably affixed to (ii) the Fc portion of an immunoglobulin, wherein the Fc portion of the immunoglobulin comprises a function-enhancing mutation, and wherein the polypeptide is water-soluble.

This invention further provides a method for treating a subject afflicted with autoimmune diabetes, comprising administering to the subject a therapeutically effective amount of the first or second polypeptide described above.

This invention further provides a method for treating a subject afflicted with graft versus host disease, comprising administering to the subject a therapeutically effective amount of the first or second polypeptide described above.

Schematic drawing of soluble ILT3 expression vector.

FIG. 2

Western Blot analysis of soluble ILT3 fusion protein.

Figure 3A:
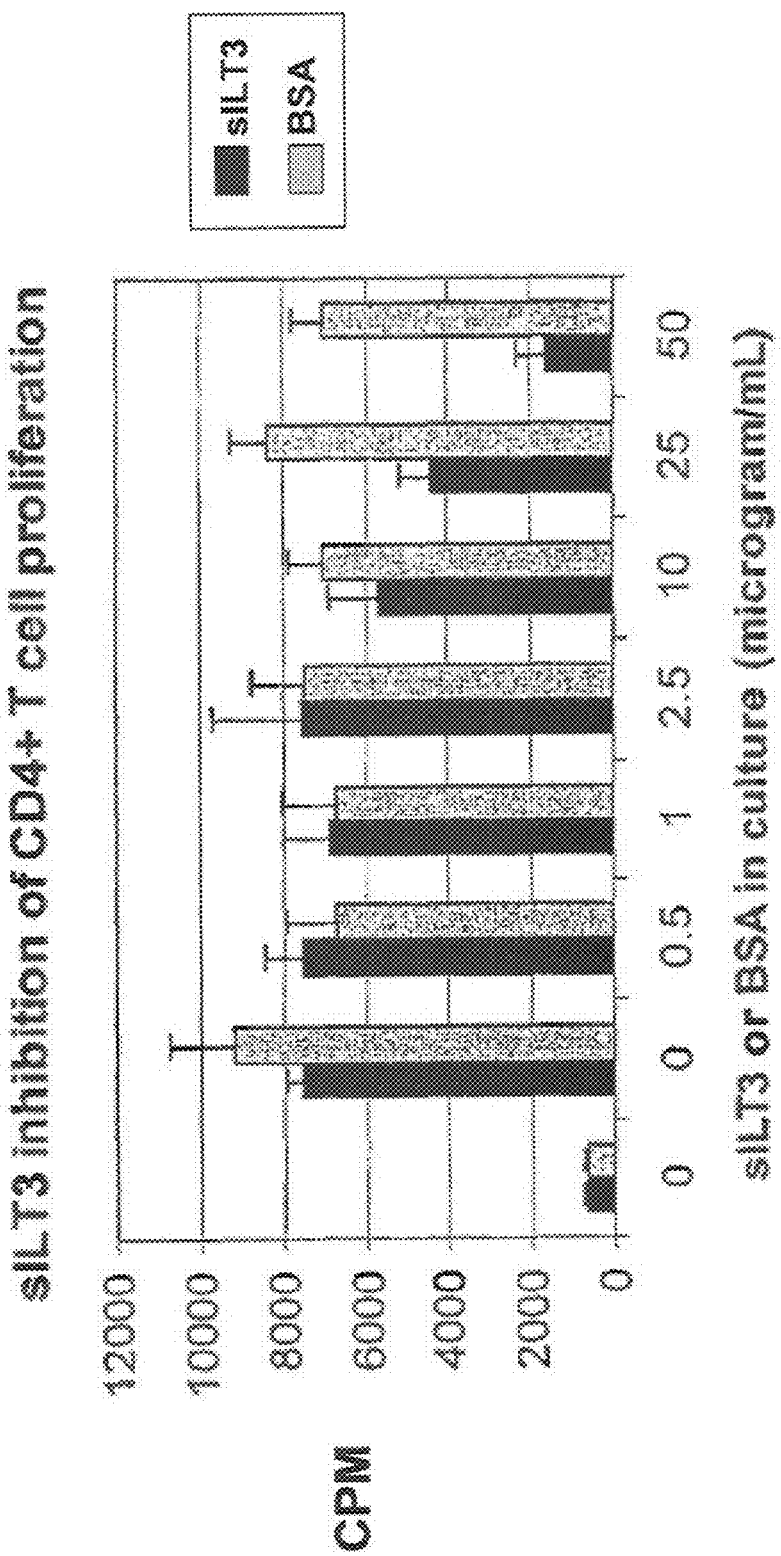
Figure 3B:
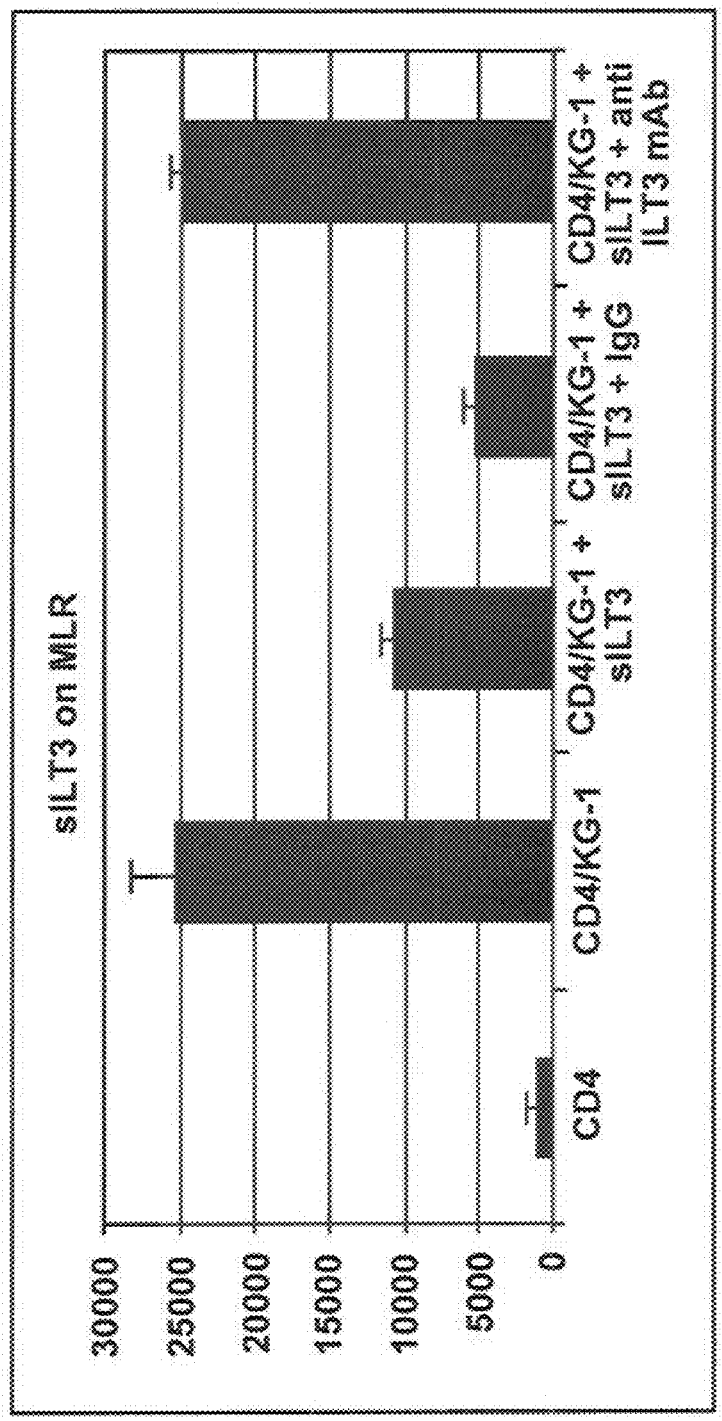

FIGS. 3A-3B (A) Soluble ILT3 inhibits T lymphocyte proliferation in vitro. (B) Inhibition is abrogated by anti-ILT3 antibody.

FIGS. 4A-4D (A) Schematic diagram of MIG retroviral expression vectors of ILT3 and ILT3 delta. (B) Fluorescence histograms of ILT3 expression on the surface of KG1.ILT3 and KG1.ILT3delta. (C) Confirmation of the molecular weight of ILT3delta by Western Blot and determination of inability of ILT3delta molecule to recruit SHP-1 by immunoprecipitation and Western blot. (D) Inhibition of protein tyrosine phosphorylation in KG1.ILT3 but not in KG1.ILT3delta cells by crosslinking anti-HLA-DR and anti-ILT3 mAbs.

Figure 5A:
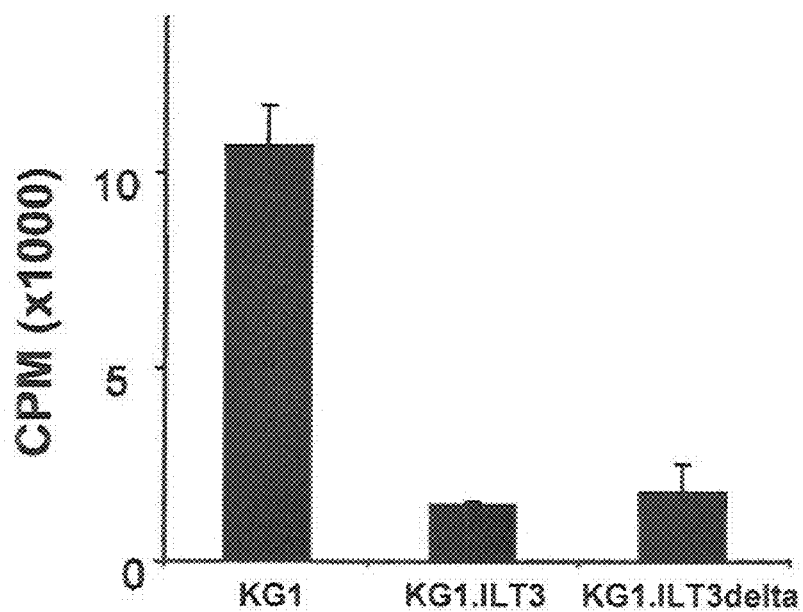
Figure 5B:
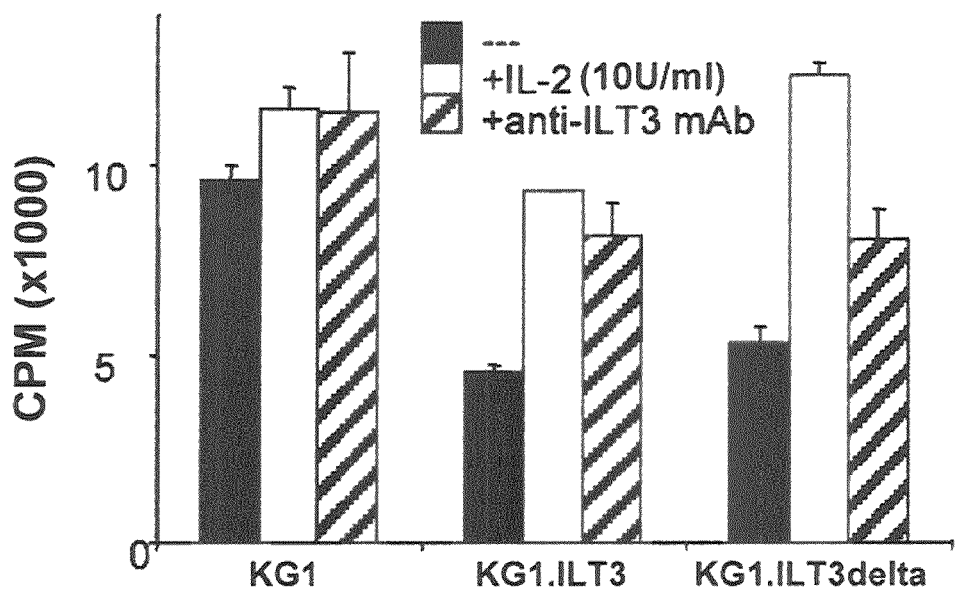
Figure 5C:
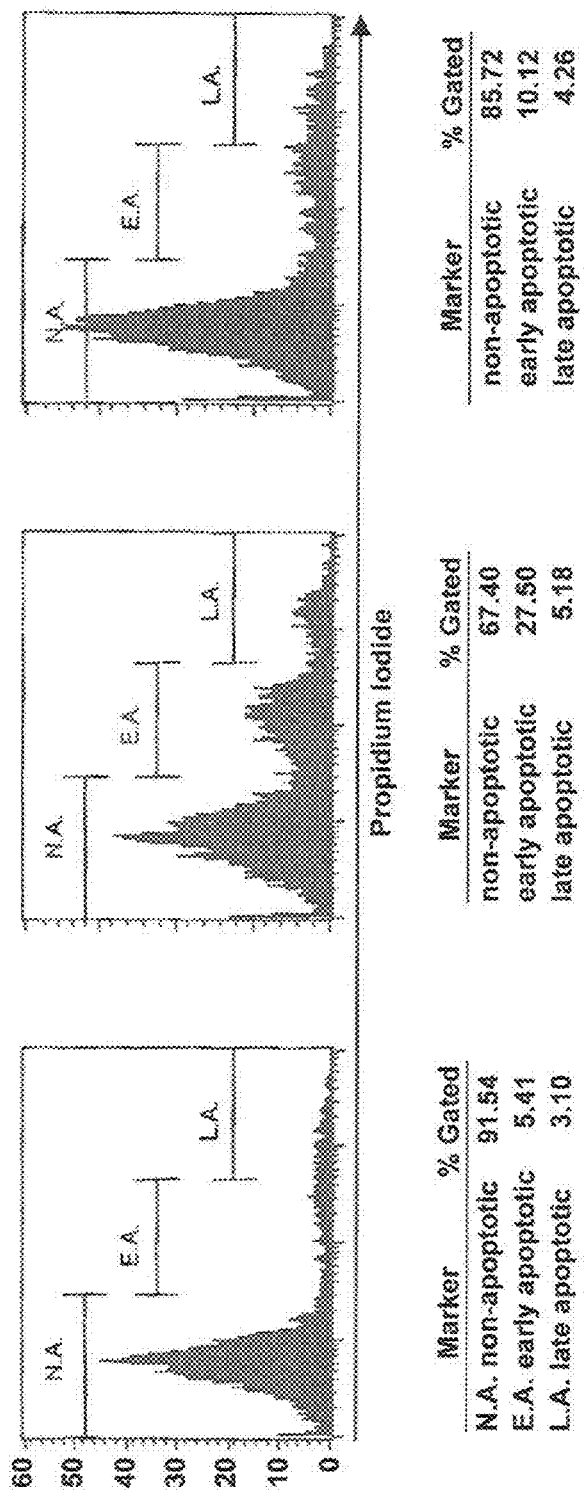

FIG. 5A-5C (A) ILT3 and ILT3delta molecules inhibit proliferation of $CD3^+CD25$-T cells in 5 day primary mixed leukocyte cultures (MLCs). (B) ILT3 and ILT3delta molecules suppress proliferation of $CD4^+$ T cells primed with KG1 cells in 3 day secondary MLC, which can be reversed by addition of IL-2 or anti-ILT3 mAb. (C) $CD8^+$ T cells primed with KG1, but not with KG1.ILT3 are cytotoxic to KG1 cells at ET ratio of 1 to 1.

FIG. 6 sILT3 suppress proliferation of $CD3^+CD25-$ T cells in primary and secondary MLCs.

FIG. 7 sILT3 inhibit generation $CD8^+$ cytotoxic T cells.

FIG. 8

Frequency of IFN-γ producing $CD8^+$ T cells from T cells primed with allogeneic APC with sILT3 is higher than $CD8^+$ T cells primed with the same APC without sILT3.

FIG. 9A-9D (A) $CD8^+$ T cells primed with allogeneic APC in the presence of sILT3, but not in the absence of sILT3 suppress proliferation response of naïve $CD3^+CD25^-$ T cells from the same responder to the original stimulator. (B) $CD8^+$ T cells primed with KG1.ILT3, but not KG1 suppress proliferation response of naïve $CD3^+CD25^-$ T cells from the same responder KG1 cells. (C) $CD8^+$ T cells primed with allogeneic APC with sILT3, but not without sILT3, or primed with KG1.ILT3 cells, but not with KG1 cells express high FOX3 protein in Western blot analysis. (D) $CD8^+$ T cells primed with allogeneic APC with sILT3, but not without sILT3 up-regulate ILT3 expression and down-regulate CD86 expression on immature DC derived from the same stimulator for priming.

FIG. 10A-10B

FITC-labeled sILT3 proteins stains allogeneic APC activated CD4+ T cells at day 3 of primary MLC culture, but not activated CD8+ T cells and naïve CD4+ and CD8+ T cells.

FIG. 11

ILT3-Fc treatment prevents islet allograft rejection in hu-NOD/SCID mice. All of the mice in the treatment group (treated with ITL-3-Fc; open circles) remained euglycemic (100% freedom from diabetes) through the study period of 91 days, indicating islet cell graft survival. By contrast, mice in the control group (IgG-treatment or no treatment; dark squares and dark circles, respectively) gradually returned to being diabetic (defined as having a blood glucose level>350 mg/dl) over the course of 3-7 weeks (days 20-50), indicating a failure of islet cell graft survival.

FIG. 12

ILT3-Fc treatment prolongs the survival time of hu-NOD/SCID islet allograft recipients independent of glycemia. Host survival time in ILT3-Fc and human IgG treated mice was calculated after exclusion of mice that rejected the islet allograft and became diabetic. Dark line indicates the percentage of surviving euglycemic mice receiving ILT3-Fc treatment (treatment group) over a period of time (0-91 days post-treatment). Light line indicates the percentage of percentage of surviving euglycemic mice receiving IgG treatment (control group).

FIG. 13

CD4+ or CD8+ T-cells sorted from mice killed on 23, 47 and 91 days following humanization were added at increasing numbers (1-8×10$^4$/well) to a fixed number (10$^4$/well) of unprimed autologous CD3+CD25− T-cells and stimulated for 6 days in MLC with irradiated, allogeneic peripheral blood mononuclear cells (PBMC) sharing HLA-A, -B, and -DR antigens with the islet transplant. Cultures were harvested after 6 days and [3H]thymidine incorporation was measured to assay T-cell reactivity.

FIG. 14

Flow cytometry analysis of human PBMC engraftment in ILT3-Fc and human IgG treated hu-NOD/SCID mice recipients of allogeneic islet cells. Mice were sacrificed on day 47. Splenocytes were stained with monoclonal antibodies raised against human CD4, CD8, CD14, CD19 and HLA.

Figure 15A:
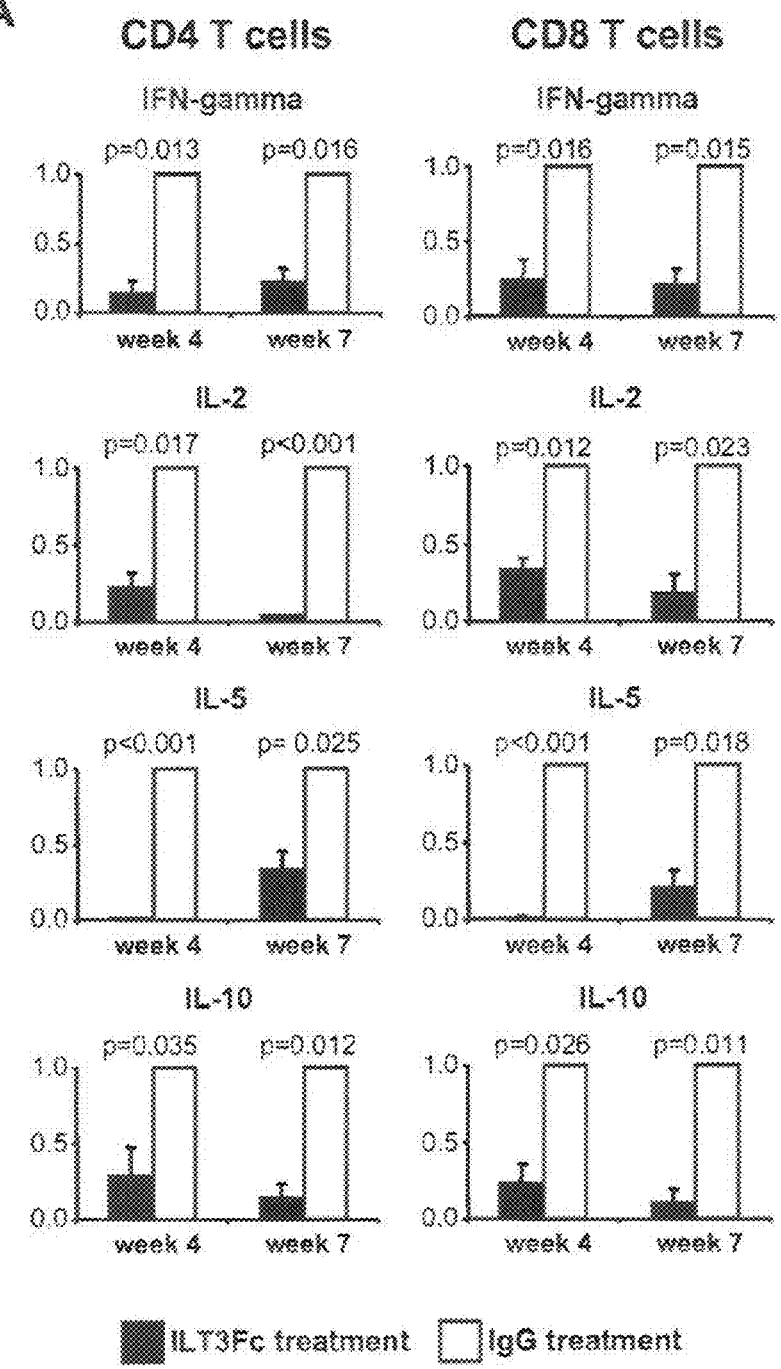
Figure 15B:
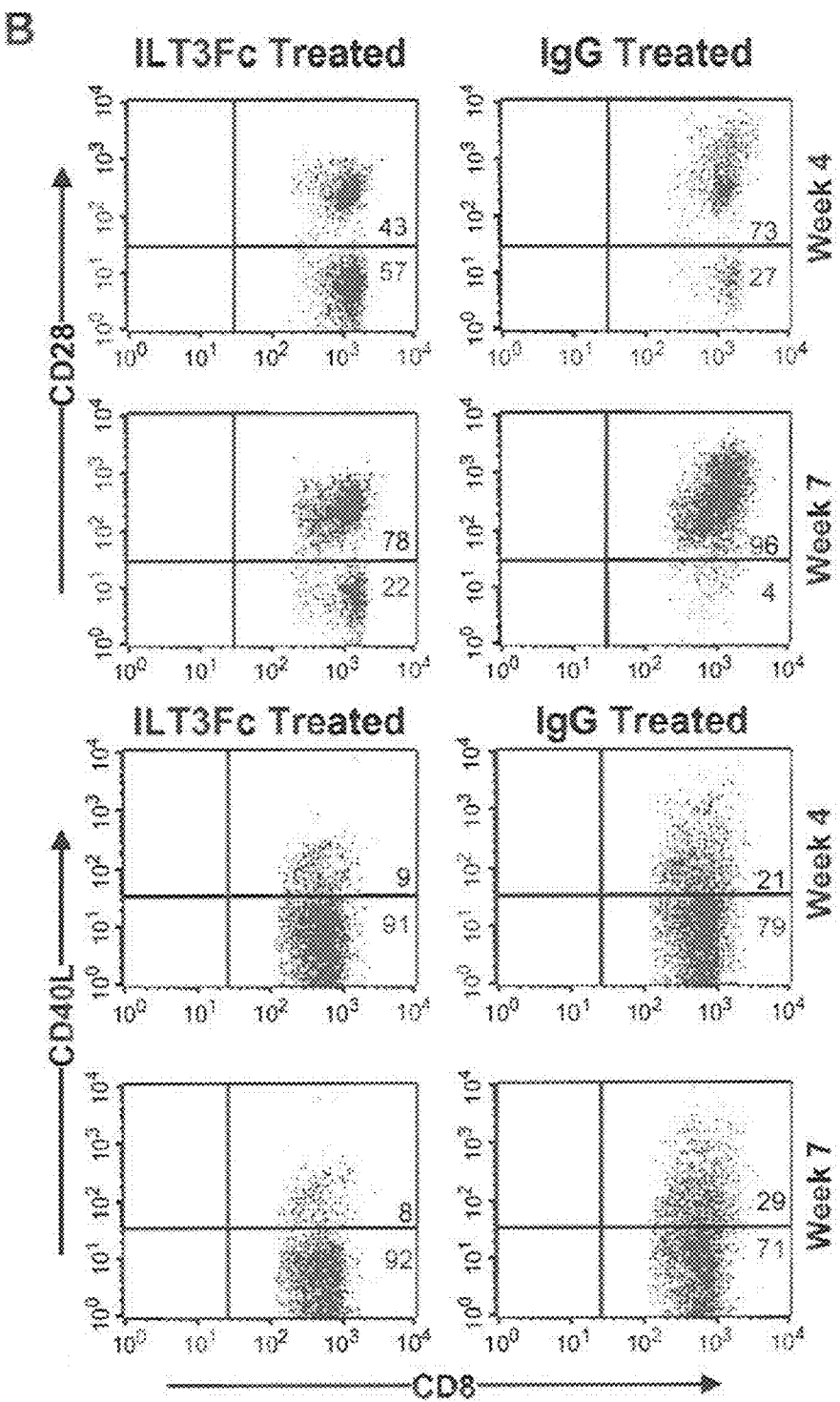

FIG. 15A-15B (A) Quantitative real-time PCR studies of cytokines (IFN-γ, IL-2, IL-5 and IL-10) expressed by human CD4+ and CD8+ T cells isolated from ILT3-Fc and IgG treated, hu-NOD/SCID recipients of islet allografts. Paired mice were sacrificed at week 4 and week 7. CD4+ and CD8+ human T cells were sorted from the spleen and analyzed by real-time PCR. (B) Flow cytometry analysis of the expression of T-cell activation markers CD28 and CD40L of human CD8+ T-cells colonizing the spleen. Paired mice were sacrificed at week 4 and week 7 and CD4+ and CD8+ human T cells were sorted from the spleen. The expression level of CD28 or CD40L was plotted against the expression level of CD8, and the abundance of CD28+ and CD28−, as well as CD40L+ and CD40L− cells was determined.

FIG. 16

Quantitative real-time PCR analysis of CD40 expression in human pancreatic islet cells. Human pancreatic islet cells were cultured 1) alone, 2) with a mixture of inflammatory cytokines, 3) with CD40L-transfected D1.1 cells, 4) with D1.1 cells plus allospecific CD8+ $T_S$ cells, or 5) with D1.1 cells plus unprimed CD8+ T cells (n=3 for all culture conditions).

FIG. 17

Immunostaining of CD8 (A-D) and CD40 (E and F) in sections of islet-engrafted kidneys from ILT3-Fc-treated (A, C, and E) and IgG-treated (B, D, and F) NOD/SCID mice 23 days after humanization.

FIG. 18

Hematoxylin and eosin (H&E) staining in sections of lung tissue from ILT3-Fc-treated (A and C) and IgG-treated (B and D) islet allograft recipients, 23 days after humanization.

FIG. 19

H&E staining (A and B) and CD8 immunostaining (C and D) in sections of islet-engrafted kidneys from ILT3-Fc-treated (A and C) and human IgG-treated (B and D) hu-NOD/SCID mouse 47 days after humanization.

FIG. 20

Immunostaining of insulin in sections of islet-engrafted kidneys from ILT3-Fc-treated (A and C) and IgG-treated (B and D) hu-NOD/SCID mice 47 days after humanization. Insulin immunostaining (E) and hematoxylin-eosin staining (F) in sections of islet-engrafted kidneys from ILT3-Fc-treated hu-NOD/SCID mice 91 days after humanization.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well known in the art. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane Antibodies: A Laboratory Manual Cold Spring Harbor Laboratory Press, Cold Spring Harbor, N.Y. (1990); Principles of Neural Science, 4$^{th}$ ed., Eric R. Kandel, James H. Schwart, Thomas M. Jessell editors. McGraw-Hill/Appleton & Lange: New York, N.Y. (2000). The nomenclatures used in connection with, and the laboratory procedures and techniques of, molecular and cellular neurobiology and medicinal and pharmaceutical chemistry described herein are those well known and commonly used in the art. Standard techniques are used for chemical syntheses, chemical analyses, pharmaceutical preparation, formulation, and delivery, and treatment of patients.

Throughout this specification, the word "comprise" or variations such as "comprises" or "comprising" will be understood to imply the inclusion of a stated integer or group of integers but not the exclusion of any other integer or group of integers.

Definitions

"Administering" shall mean delivering in a manner which is effected or performed using any of the various methods and delivery systems known to those skilled in the art. Administering can be performed, for example, topically, intravenously, pericardially, orally, via implant, transmucosally, transdermally, intradermally, intramuscularly, subcutaneously, intraperitoneally, intrathecally, intralymphatically, intralesionally, or epidurally. Administering can also be performed, for example, once, a plurality of times, and/or over one or more extended periods.

"Agent" shall include, without limitation, an organic or inorganic compound, a nucleic acid, a polypeptide, a lipid, a carbohydrate or a physical stimulus. Agents include, for example, agents which are known with respect to structure and/or function, and those which are not known with respect to structure or function.

"Concurrent" administration of two agents shall mean administration wherein the time period over which the first agent is administered either overlaps with, or is coincident with, the time period over which the second agent is administered. For example, a first and a second agent are concurrently administered if the first agent is administered once per week for four weeks, and the second agent is administered twice per week for the first three of those four weeks. Likewise, for example, a first and second agent are concurrently administered if the first and second agent are each administered, in the same or separate pills, on the same day, once per week for four weeks.

"Delaying" the onset of a disorder shall mean slowing the progression of the disorder, or extending the time before the onset begins.

"Engraftment" shall mean the incorporation of grafted (i.e., transplanted) tissue or cells into the body of the host, or the process of transplanted stem cells reproducing new cells.

"Expression vector" shall mean a nucleic acid encoding a nucleic acid of interest and/or a protein of interest, which nucleic acid, when placed in a cell, permits the expression of the nucleic acid or protein of interest. Expression vectors are well known in the art.

"Extracellular domain of ILT3" shall mean the N-terminal 258 amino acid residues of ILT3 (e.g., human ILT3 having the sequence of GenBank Accession No. U82979). A "portion" of the extracellular domain of ILT3 includes, for example, the IgG1-like domain 1 (residues 42-102 of human ILT3), the IgG1-like domain 2 (residues 137-197 of human ILT3), and the N-terminal 250, 240, 230, 220, 210, 200, 190, 180, 170, 160 or 150 amino acid residues of ILT3.

"Function-enhancing mutation", with respect to the second polypeptide of this invention, shall mean any mutation which confers a physical property (e.g., reduced binding of the Fc moiety to an Fc receptor) to the polypeptide which permits it to better accomplish its therapeutic role (e.g., through increasing its half-life or reducing adverse effects otherwise caused by a subject's immune system).

"Humanization", with respect to mice, shall mean the injection and subsequent incorporation, or engraftment, of human haematopoietic stem cells or peripheral blood mononuclear cells (PBMC) into immunodeficient mice.

"Humanized mice" shall mean immunodeficient mice injected (i.e., engrafted) with human haematopoietic stem cells or PBMC.

"ILT3" shall mean the gene, mRNA, or protein of "Immunoglobulin-Like Transcript-3", and is synonymous with "ILT-3", "LIR-5", "CD85K" and "LILRB4". The mRNA coding sequence for human ILT3 is provided under GenBank No. U82979.

"Immunoglobulin" and "antibody" are used synonymously herein, and shall include, by way of example, both naturally occurring and non-naturally occurring antibodies. Specifically, this term includes polyclonal and monoclonal antibodies, and antigen-binding fragments (e.g., Fab fragments, as opposed to Fc fragments) thereof. Furthermore, this term includes chimeric antibodies (e.g., humanized antibodies) and wholly synthetic antibodies, and antigen-binding fragments thereof. Within the scope of the term "antibody" are also antibodies that have been modified in sequence, but remain capable of specific binding to an antigen. Example of modified antibodies are interspecies chimeric and humanized antibodies; antibody fusions; and heteromeric antibody complexes, such as diabodies (bispecific antibodies), single-chain diabodies, and intrabodies (see, e.g., Marasco (ed.), Intracellular Antibodies: Research and Disease Applications, Springer-Verlag New York, Inc. (1998) (ISBN: 3540641513), the disclosure of which is incorporated herein by reference in its entirety).

"Inhibiting" the onset of a disorder shall mean either lessening the likelihood of the disorder's onset, delaying the disorder's onset, or preventing the onset of the disorder entirely. In the preferred embodiment, inhibiting the onset of a disorder means preventing its onset entirely.

"Islets" shall mean a composition comprising pancreatic islets, which is synonymous with the islets of Langehaus, which is the cluster of cells in which the endocrine cells (that produce, e.g., insulin) are grouped.

"Islet cells" shall mean a composition comprising pancreatic islet cells, i.e., cells from the islets of Langehaus, which is the cluster of cells in which the endocrine cells (that produce, e.g., insulin) are grouped.

"Mammalian cell" shall mean any mammalian cell. Mammalian cells include, without limitation, cells which are normal, abnormal and transformed, and are exemplified by neurons, epithelial cells, muscle cells, blood cells, immune cells, stem cells, osteocytes, endothelial cells and blast cells.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Operably affixed", with respect to the second polypeptide of this invention, shall mean affixed (e.g., via peptide bond) in a manner permitting the ILT3 moiety thereof to inhibit the proliferation of CD4$^+$ T cells. In one embodiment, a polypeptide linker of 10, 11, 12, 13, 14, 15 or 16 amino acid residues in length is used to join the ILT3 and Fc moieties.

"Pharmaceutically acceptable carriers" are well known to those skilled in the art and include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Porphyrin or Lipofectin may also be used as a delivery agent. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

"Polypeptide" and "protein" are used interchangeably herein, and each means a polymer of amino acid residues. The amino acid residues can be naturally occurring or chemical analogues thereof. Polypeptides and proteins can also include modifications such as glycosylation, lipid attachment, sulfation, hydroxylation, and ADP-ribosylation. A variety of methods for labeling polypeptides and substituents or labels useful for such purposes are well known in the art, and include radioactive isotopes such as $^{125}$I, $^{32}$P, $^{35}$S, and $^{3}$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., 1992, hereby incorporated by reference.

"Prophylactically effective amount" means an amount sufficient to inhibit the onset of a disorder or a complication associated with a disorder in a subject. "Subject" shall mean any organism including, without limitation, a mammal such as a mouse, a rat, a dog, a guinea pig, a ferret, a rabbit and a primate. In the preferred embodiment, the subject is a human being.

"Therapeutically effective amount" means any amount of an agent which, when administered to a subject afflicted with a disorder against which the agent is effective, causes the subject to be treated.

"Transplant rejection" shall mean the adverse response by the immune system of a subject who has received a transplant (e.g., of an organ or tissue). Transplanted organs in this context include, for example, heart, kidney, skin, lung, liver, eye and bone. Transplanted tissue in this context includes, for example, vascular tissue.

"Treating" a subject afflicted with a disorder shall mean causing the subject to experience a reduction, delayed progression, regression or remission of the disorder and/or its symptoms. In one embodiment, recurrence of the disorder and/or its symptoms is prevented. In the preferred embodiment, the subject is cured of the disorder and/or its symptoms.

This invention provides a first polypeptide comprising all or a portion of the extracellular domain of ILT3, wherein the polypeptide is water-soluble and does not comprise the Fc portion of an immunoglobulin.

In one embodiment, the polypeptide is isolated. In a further embodiment, the polypeptide comprises the extracellular domain of ILT3. In yet a further embodiment, the polypeptide consists of the extracellular domain of ILT3. Preferably, the ILT3 is human ILT3. In one embodiment, the portion of ILT3 is the IgG1-like domain 1, the IgG1-like domain 2 or the N-terminal 250, 240, 230, 220, 210, 200, 190, 180, 170, 160 or 150 amino acid residues of ILT3. In another embodiment, the portion of the ILT3 is capable of inhibiting T cell proliferation or inducing differentiation of a T cell into a regulatory T cell. Assays to detect T cell proliferation and differentiation into regulatory T cells are well known in the art and include those described below. Such polypeptides are useful for preventing, inhibiting, reducing or suppressing immune responses mediated by the activation of T cells.

Also contemplated are polypeptides of the invention which contain minor variations provided that the variations in the amino acid sequence maintain at least 75%, more preferably at least 80%, 90%, 95%, and most preferably 99% sequence identity and the molecule retains bioactivity (e.g., inhibition of T cell proliferation, differentiation of T cells into regulatory T cells, suppression of immune responses mediated by activated T cells). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family.

This invention also provides a second polypeptide comprising (i) all or a portion of the extracellular domain of ILT3 operably affixed to (ii) the Fc portion of an immunoglobulin, wherein the Fc portion of the immunoglobulin comprises a function-enhancing mutation, and wherein the polypeptide is water-soluble. The Fc portion may also be substituted with any other peptide that promotes dimerization or oligomerization. For example, the peptide may comprise cysteine residues that form disulfide bonds or other residues that promote covalent or nonconvalent interactions between the peptides such that the peptides mediate dimerization or oligomerization. Suitable peptides include leucine zippers (e.g., those derived from the yeast GCN4 or a modified version thereof. Other exemplary oligomerization domains are described in, e.g., WO 00/69907, WO 99/62953, WO 98/56906, WO 98/18943, and WO 96/37621.

In one embodiment, the polypeptide is isolated. In a further embodiment, the polypeptide comprises the extracellular domain of ILT3. Preferably, the ILT3 is human ILT3. In a further embodiment, the Fc portion of the immunoglobulin is the Fc portion of IgG1. Preferably, the IgG1 is human IgG1. In a further embodiment, the function-enhancing mutation in the Fc portion of the immunoglobulin inhibits the binding of the Fc portion of an immunoglobulin to an Fc receptor. In one example, the function-enhancing mutation in the Fc portion of the immunoglobulin is an Asn-->Gln point mutation at amino acid residue 77 of the Fc portion of human IgG1.

This invention further provides a third polypeptide comprising (i) all or a portion of the extracellular domain of ILT3 operably affixed to (ii) a transmembrane domain.

In one embodiment the transmembrane domain corresponds to or is derived from the transmembrane domain of human ILT3 (e.g., amino acid residues 259 to 280 of the sequence of GenBank Accession No. U82979). In another embodiment, the transmembrane domain is derived from a protein other than human ILT3 wherein the protein comprises a transmembrane domain. Nucleic acids encoding these polypeptides, expression vectors and host cells comprising the nucleic acids and methods for producing these polypeptides are also provided.

Also contemplated are polypeptides of the invention which contain minor variations provided that the variations in the amino acid sequence maintain at least 75%, more preferably at least 80%, 90%, 95%, and most preferably 99% sequence identity and the molecule retains bioactivity (e.g., inhibition of T cell proliferation, differentiation of T cells into regulatory T cells, suppression of immune responses mediated by activated T cells). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family.

This invention provides a first isolated nucleic acid which encodes a polypeptide comprising all or a portion of the extracellular domain of ILT3, wherein the polypeptide is water-soluble and does not comprise the Fc portion of an immunoglobulin. This invention includes nucleic acids encoding polypeptides of the invention containing a conservative mutation as described above.

This invention further provides a second isolated nucleic acid which encodes a polypeptide comprising (i) all or a portion of the extracellular domain of ILT3 operably affixed to (ii) the Fc portion of an immunoglobulin, wherein the Fc portion of the immunoglobulin comprises a function-enhancing mutation, and wherein the polypeptide is water-soluble.

In one embodiment of the instant nucleic acids, the nucleic acids are DNA (e.g., cDNA). In a further embodiment, the nucleic acids are RNA.

This invention provides a first expression vector comprising a nucleic acid sequence encoding a polypeptide comprising all or a portion of the extracellular domain of ILT3, wherein the polypeptide is water-soluble and does not comprise the Fc portion of an immunoglobulin.

This invention further provides a second expression vector comprising a nucleic acid sequence encoding a polypeptide comprising (i) all or a portion of the extracellular domain of ILT3 operably affixed to (ii) the Fc portion of an immunoglobulin, wherein the Fc portion of the immunoglobulin comprises a function-enhancing mutation, and wherein the polypeptide is water-soluble.

This invention provides a first host vector system which comprises the first expression vector and a suitable host cell.

This invention further provides a second host vector system which comprises the second expression vector and a suitable host cell.

The polypeptides of the invention may be expressed using any suitable vector. Typically, the vectors are derived from virus, plasmid, prokaryotic or eukaryotic chromosomal elements, or some combination thereof, and may optionally include at least one origin of replication, at least one site for insertion of heterologous nucleic acid, and at least one selectable marker. The invention also contemplates expressing the polypeptides of the invention using artificial chromosomes, e.g., bacterial artificial chromosomes (BACs), yeast artificial chromosomes (YACs), mammalian artificial chromosomes (MACs), and human artificial chromosomes (HACs), e.g., when it is necessary to propagate nucleic acids larger than can readily be accommodated in viral or plasmid vectors.

The vectors will also often include elements that permit in vitro transcription of RNA from the inserted heterologous nucleic acid. Such vectors typically include a phage promoter, such as that from T7, T3, or SP6, flanking the nucleic acid insert. Expression vectors often include a variety of other genetic elements operatively linked to the protein-encoding heterologous nucleic acid insert, typically genetic elements that drive and regulate transcription, such as promoters and enhancer elements, those that facilitate RNA processing, such as transcription termination, splicing signals and/or polyadenylation signals, and those that facilitate translation, such as ribosomal consensus sequences. Other transcription control sequences include, e.g., operators, silencers, and the like. Use of such expression control elements, including those that confer constitutive or inducible expression, and developmental or tissue-regulated expression are well-known in the art.

Expression vectors can be designed to fuse the expressed polypeptide to small protein tags that facilitate purification and/or visualization. Many such tags are known and available. Expression vectors can also be designed to fuse proteins encoded by the heterologous nucleic acid insert to polypeptides larger than purification and/or identification tags. Useful protein fusions include those that permit display of the encoded protein on the surface of a phage or cell, fusions to intrinsically fluorescent proteins, such as luciferase or those that have a green fluorescent protein (GFP)-like chromophore, and fusions for use in two hybrid selection systems.

For long-term, high-yield recombinant production of the proteins, protein fusions, and protein fragments described herein, stable expression is preferred. Stable expression is readily achieved by integration into the host cell genome of vectors (preferably having selectable markers), followed by selection for integrants.

The polypeptides of the invention may be expressed in any appropriate host cell. The host cell can be prokaryotic (bacteria) or eukaryotic (e.g., yeast, insect, plant and animal cells). A host cell strain may be chosen for its ability to carry out desired post-translational modifications of the expressed protein. Such post-translational modifications of the polypeptide include, but are not limited to, acetylation, carboxylation, glycosylation, phosphorylation, hydroxylation, sulfation, lipidation, and acylation.

Exemplary prokaryotic host cells are *E. coli, Caulobacter crescentus, Streptomyces* species, and *Salmonella typhimurium* cells. Exemplary yeast host cells are *Saccharomyces cerevisiae, Schizosaccharomyces pombe, Pichia pastoris*, and *Pichia methanolica*. Exemplary insect host cells are those from *Spodoptera frugiperda* (e.g., Sf9 and Sf21 cell lines, and EXPRESSF™ T cells (Protein Sciences Corp., Meriden, Conn., USA)), *Drosophila* S2 cells, and *Trichoplusia ni* HIGH FIVE® Cells (Invitrogen, Carlsbad, Calif., USA). Exemplary mammalian host cells are COS1 and COS7 cells, NSO cells, Chinese hamster ovary (CHO) cells, NIH 3T3 cells, 293 cells, HEPG2 cells, HeLa cells, L cells, MDCK, HEK293, WI38, murine ES cell lines (e.g., from strains 129/SV, C57/BLG, DBA-1, 129/SVJ), K562, Jurkat cells, BW5147 and any other commercially available human cell lines. Other useful mammalian cell lines are well known and readily available from the American Type Culture Collection (ATCC) (Manassas, Va., USA) and the National Institute of General Medical Sciences (NIGMS) Human Genetic Cell Repository at the Coriell Cell Repositories (Camden, N.J., USA).

In one embodiment of the instant host vector systems, the host cell is a eukaryotic, bacterial, insect or yeast cell. In a further embodiment, the host cell is a eukaryotic cell (e.g., a mammalian cell).

This invention provides a method for producing the first polypeptide, comprising (a) culturing the first host vector system under conditions permitting polypeptide synthesis by the host vector system, and (b) recovering the polypeptide so produced.

This invention also provides a method for producing the second polypeptide, comprising (a) culturing the second host vector system under conditions permitting polypeptide synthesis by the host vector system, and (b) recovering the polypeptide so produced.

This invention provides a first composition comprising (a) a pharmaceutically acceptable carrier and (b) the first polypeptide.

This invention further provides a second composition comprising (a) a pharmaceutically acceptable carrier and (b) the second polypeptide.

The polypeptides of the invention are administered to a subject via parenteral injection (e.g., subcutaneous, intradermal, intraperitoneal, and intravenous). The polypeptides of the invention are administered, for example, once, a plurality of times, and/or over one or more extended periods. They may be administered alone or in pharmaceutical compositions.

The polypeptides of the invention have immunosuppressive activity, which act on T cells only upon their activation. Thus, these polypeptides induce antigen-specific tolerance. The polypeptides and compositions of the invention are useful for preventing, inhibiting, suppressing or reducing an immune response mediated by antigen-specific activation of T cells. In one embodiment, the immune response is involved in transplant rejection. In another embodiment, the immune response is associated with an autoimmune disease, hypersensitivity or allergy. In yet another embodiment, the immune response is related to an inflammatory disorder.

This invention provides a method for inhibiting the onset of transplant rejection in a subject who has received, or is about to receive, a transplant, comprising administering to the subject a prophylactically effective amount of the first, second or third polypeptide.

This invention further provides a method for treating transplant rejection in a subject who has received a transplant, comprising administering to the subject a therapeutically effective amount of the first, second or third polypeptide.

In certain embodiments of the methods for inhibiting the onset of and treating transplant rejection, the transplant is an organ transplant. In other embodiments, the transplant is a tissue transplant or involves the transplantation of cells. Transplanted organs include, for example, pancreas heart, kidney, skin, lung, liver, eye, bone, and bone marrow. Transplanted tissue includes, for example, vascular tissue and islets. Transplanted cells include stem cells, e.g., umbilical cord stem cells or adult stem cells, pancreatic islet cells, epithelial cells, endothelial cells, and liver cells. The transplant may also be a prosthetic device, e.g., stent. The transplant may be xenogeneic or allogeneic. In one embodiment, the subject is a mammal. Preferably, the subject is a human.

In certain embodiments, the transplant is an islet transplant. The islets can be transplanted by injection under the kidney capsules; however, other cell, tissue, and organ transplantation paradigms well known in the art can be used. It is contemplated that the immunotherapeutic function of the present immunotolerance induction regimen can be applied to transplantation of all or part of the pancreas as well as to the transplantation of pancreatic islets or islet cells. The donor can be a cadaver or a living donor. Furthermore, the donor can be of the same species as the subject being treated or a different species than the subject being treated. Thus, using the method of the invention, transplantation can be performed across species (i.e., xenogeneic transplantation or xenograft) and within the same species (i.e., allogeneic transplantation or allograft).

In one embodiment, the polypeptide is administered concurrently with a second immunosuppressive agent, such as cyclosporine, OKT3 Antibody, rapamycin, Campath I, anti-CD69 antibody, thymoglobulin, and anti-thymocytic antibody. The polypeptide may also be administered before or after administration of the second immunosuppressive agent. In another embodiment, the polypeptide is administered to the subject at the time of transplantation and twice a week for two weeks as is routine for transplants. In another embodiment, the polypeptide is administered to the subject at the onset of or during rejection.

Symptoms associated with rejection of a transplant are well known in the art and include increased blood urea nitrogen (BUN) levels for kidney, increased glycemia for pancreas, lymphocyte infiltrates for heart, and increased levels of enzymes such as aspartate aminotransferase (SGOT) and alanine aminotransferase (SGPT) for liver.

Histological indications of rejection of an islet transplant are well known in the art and include insulitis (infiltration of islets by CD8+ T-cells), diffuse membrane immunostaining of CD40, and presence of scattered apoptotic bodies in the islets.

This invention provides a method for treating a subject afflicted with an autoimmune disorder, comprising administering to the subject a therapeutically effective amount of the first, second or third polypeptide.

The autoimmune disorder treated can be any such disorder, and includes, without limitation, rheumatoid arthritis, Crohn's disease, multiple sclerosis, autoimmune diabetes, systemic lupus erythematosus, lupus vulgaris, thyroiditis, Addison's Disease, hemolytic anemia, antiphospbolipid syndrome, dermatitis, allergic encephalomyelitis, glomerulonephritis, Goodpasture's Syndrome, Graves' Disease, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Pulmonary Inflammation, Guillain-Barre Syndrome, and autoimmune inflammatory eye disease. In one embodiment, the subject is a mammal. Preferably, in the subject method, the subject is human. In one embodiment, the polypeptide is administered to the subject during a flare-up of an autoimmune attack. The method may further comprise administration of additional immunosuppressive drugs, e.g., cytotoxic agents, cyclosporine, methotrexate, azathioprine, and corticosteroids.

Similarly, allergic reactions and conditions, such as asthma (particularly allergic asthma) or other respiratory problems, may also be treated by a polypeptide of the present invention. These molecules can be used to treat anaphylaxis, hypersensitivity to an antigenic molecule, or blood group incompatibility.

This invention further provides a method for treating a subject afflicted with an inflammatory disorder, comprising administering to the subject a therapeutically effective amount of the first, second or third polypeptide.

The inflammatory disorder treated can be any such disorder, and includes, without limitation, (i) inflammatory diseases such as chronic inflammatory pathologies (including chronic inflammatory pathologies such as, but not limited to, sarcoidosis, chronic inflammatory bowel disease, ulcerative colitis, and Crohn's pathology); (ii) vascular inflammatory pathologies such as, but not limited to, disseminated intravascular coagulation, atherosclerosis, Kawasaki's pathology and vasculitis syndromes (such as, but not limited to, polyarteritis nodosa, Wegener's granulomatosis, Henoch-Schonlein purpura, giant cell arthritis and microscopic vasculitis of the kidneys); (iii) chronic active hepatitis; (iv) Sjogren's syndrome; (v) spondyloarthropathies such as ankylosing spondylitis, psoriatic arthritis and spondylitis, enteropathic arthritis and spondylitis, reactive arthritis and arthritis associated with inflammatory bowel disease; and (vi) uveitis. Preferably, in the subject method, the subject is human. The method can also be combined with administration of additional anti-inflammatory agents. Anti-inflammatory agents include, but are not limited to, any known nonsteroidal anti-inflammatory agent such as, salicylic acid derivatives (aspirin), para-aminophenol derivatives (acetaminophen), indole and indene acetic acids (indomethacin), heteroaryl acetic acids (ketorolac), arylpropionic acids (ibuprofen), anthranilic acids (mefenamic acid), enolic acids (oxicams) and alkanones (nabumetone) and any known steroidal anti-inflammatory agent which include corticosteriods and biologically active synthetic analogs with respect to their relative glucocorticoid (metabolic) and mineralocorticoid (electrolyte-regulating) activities. Additionally, other drugs used in the therapy of inflammation include, but are not limited to, autocoid antagonists such as histamine, bradykinin receptor antagonists, leukotriene and prostaglandin receptor antagonists, and platelet activating factor receptor antagonists.

This invention further provides a method for inducing anergy in a T cell, thereby causing it to differentiate into a regulatory cell, comprising contacting the T cell with the first, second or third polypeptide under conditions permitting priming of the T cell to occur, thereby inducing anergy in the T cell and causing it to differentiate into a regulatory cell. Contacting of the T cell may be performed in vivo, ex vivo or in vitro.

In one embodiment, the T cell is a $CD4^+$ T cell, a $CD3^+$ cell or a $CD8^+$ T cell, and the conditions permitting priming to occur comprise contacting the T cell with an allogeneic stimulator (e.g., an allogeneic antigen presenting cell (APC)) or an autologous APC that has been pulsed with an antigen. Exemplary antigen presenting cells include dendritic cells, monocytes, macrophages, endothelial cells and epithelial cells. In the preferred embodiment, the allogeneic stimulator is an irradiated KG1 cell.

This invention further provides a method for treating a subject afflicted with an autoimmune disorder, comprising contacting, ex vivo, the first, second or third polypeptide with T cells obtained from the subject, wherein the contacting is performed under conditions permitting priming of the cells to occur, and intravenously administering the resulting cells to the subject, so as to treat the subject.

This invention also provides a method for treating transplant rejection in a subject, comprising the steps of contacting, ex vivo, T cells obtained from the subject with a polypeptide of the invention (e.g. the first, second or third polypeptide) under conditions permitting priming of the cells, and administering the resulting cells to the subject.

Methods of treating inflammatory disease or graft versus host disease in a subject by treating T cells obtained from the subject with a polypeptide of the invention ex vivo and then administering the treated T cells to the subject are also contemplated.

In one embodiment, the T cell is a $CD4^+$ T cell, a $CD3^+$ T cell or a $CD8^+$ T cell and the conditions permitting priming to occur comprise contacting the T cell with an allogeneic stimulator (e.g., an allogeneic antigen presenting cell (APC)) or an autologous APC that has been pulsed with an antigen. Exemplary antigen presenting cells include dendritic cells, monocytes, macrophages, endothelial and epithelial cells. In the preferred embodiment, the allogeneic stimulator is an irradiated KG1 cell.

Determining an effective amount of the instant polypeptides for use in the instant invention can be done based on animal data using routine computational methods. In one embodiment, the effective amount, administered intravenously, is between about 0.5 mg/kg and about 50 mg/kg of polypeptide. In another embodiment, the effective amount, administered intravenously, is between about 1 mg/kg and about 20 mg/kg of polypeptide. In the preferred embodiment, the effective amount, administered intravenously, is about 3, 5 or 10 mg/kg of polypeptide.

In one embodiment of the instant methods, the polypeptide is administered in a single dose. In another embodiment, the polypeptide is administered in multiple doses.

Determination of a preferred pharmaceutical formulation and a therapeutically efficient dose regiment for a given application is within the skill of the art taking into consideration, for example, the condition and weight of the patient, the extent of desired treatment and the tolerance of the patient for the treatment.

Administration of the polypeptides or compositions of this invention, including isolated and purified forms, may be accomplished using any of the conventionally accepted modes of administration of agents which are used to prevent or treat transplantation rejection or to treat autoimmune or inflammatory disorders.

The pharmaceutical compositions of this invention may be in a variety of forms, which may be selected according to the preferred modes of administration. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The compositions of this invention may, for example, be placed into sterile, isotonic formulations with or without cofactors which stimulate uptake or stability. The formulation is preferably liquid, or may be lyophilized powder. For example, the compositions or polypeptides of the invention may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions of the present invention can also be formulated so as to provide slow or controlled-release of the active ingredient therein using, e.g., hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a composition capable of releasing the active ingredient at the required rate to maintain constant pharmacological activity for a desirable period of time. Such dosage forms can provide a supply of a drug to the body during a predetermined period of time and thus maintain drug levels in the therapeutic range for longer periods of time than other non-controlled formulations.

Also provided are methods of delivering membrane-bound polypeptides of the invention using lipid bilayers or by administration of cells manipulated to express the polypeptides of the invention (e.g., cells transfected with a nucleic acid encoding a polypeptide of the invention) (M. Davis et al., JCB 166:579-590 (2004)).

Nucleic acids encoding a polypeptide of the invention may be administered using gene therapy methods. Retrovirus vectors and adeno-associated virus (AAV) vectors are preferred vectors according to the invention for transferring nucleic acids encoding the polypeptides of the invention into cells in vivo, particularly into human cells. These vectors provide efficient delivery of genes into cells, and the transferred nucleic acids are stably integrated into the chromosomal DNA of the host. The development of specialized cell lines ("packaging cells") that produce replication-defective retroviruses are especially preferred for gene therapy applications (see, e.g., Miller, A. D. Blood 76:271 (1990)). Recombinant retrovirus may be constructed in which part of the retroviral coding sequence (gag, pol, env) has been replaced by nucleic acid encoding one of the subject receptors rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses may be found, e.g., in Current Protocols in Molecular Biology, Ausubel, F. M. et al. (eds.) Greene Publishing Associates, (1989), Sections 9.10-9.14 and other standard laboratory manuals. Representative examples of retroviruses include pLJ, pZIP, pWE and pEM which are well known to those skilled in the art. Representative examples of packaging virus lines for preparing both ecotropic and amphotropic retroviral systems include psi.Crip, psi.Cre, psi 2 and psi.Am. Retroviruses have been widely used to introduce a variety of genes into many different cell types in vitro and/or in vivo. Moreover, it is useful to limit the infection spectrum of retroviruses and retroviral-based vectors by modifying the viral packaging proteins on the surface of the viral particle (see, for example PCT publications WO93/25234 and WO94/06920; Roux et al. PNAS 86:9079-9083 (1989); Julan et al. J. Gen Virol 73:3251-3255 (1992); and Goud et al. Virology 163: 251-254 (1983)); Neda et al. J. Biol Chem 266:14143-14146 (1991)).

This invention further provides an article of manufacture comprising (a) a packaging material having therein the first polypeptide, and (b) a label indicating a use for the polypeptide for (i) treating or inhibiting the onset of transplant rejection in a subject, (ii) treating an autoimmune disorder in a subject, or (iii) treating an inflammatory disorder in a subject.

Finally, this invention provides an article of manufacture comprising (a) a packaging material having therein the second polypeptide, and (b) a label indicating a use for the polypeptide for (i) treating or inhibiting the onset of transplant rejection in a subject, (ii) treating an autoimmune disorder in a subject, or (iii) treating an inflammatory disorder in a subject.

This invention provides a method for inhibiting the onset of, or treating, transplant rejection in a subject who has received, or is about to receive, a pancreatic islet cell transplant by administering the polypeptide to the subject.

This invention provides a method for inhibiting the onset of, or treating, autoimmune diabetes by administering the polypeptide to the subject.

This invention provides a method for inhibiting the onset of, or treating, Graft Versus Host Disease (GVHD) by administering the polypeptide to the subject.

This invention will be better understood from the Experimental Details which follow. However, one skilled in the art will readily appreciate that the specific methods and results discussed are merely illustrative of the invention as described more fully in the claims which follow thereafter.

Experimental Details

The most extensively studied "protein therapeutic drugs" are (1) monoclonal antibodies, (2) cytokine-fusion proteins and (3) chimeric cell adhesion molecules that prevent T cell activation and/or proliferation.

Soluble ILT3

Soluble ILT3 ("sILT3") (encompassing the first and second instant polypeptides) belongs to the family of chimeric proteins that modulate the immune system. sILT3 is an attractive candidate for therapeutic use based on its potent in vitro immune modulating activities and orthologue (homolog) of ILT3 studies shown in animal models of acute and chronic inflammation, autoimmunity. Soluble ILT3 induces immune tolerance by inhibition of T cell activation that contributes to graft rejection.

Examples of soluble chimeric proteins being investigated as therapeutic agents in clinical trials are CTLA-4, CD86, PD-1 and PD-L1 fusion proteins. Protein therapeutics are administered through a parenteral route, e.g., subcutaneous, intravenous, intradermal, or intraperitoneal routes. Some have been proven effective against specific autoimmune disease. However, these molecules behave both stimulatory and inhibitory manner depending on their counter-receptors. Furthermore, their expression is ubiquitous such that CTLA-4 and its counter-receptor are expressed on the same T cells. Moreover, the broad expression pattern of their counter-receptors on B cell, DCs, ECs, macrophages, fibroblasts, muscle cells and trophoblast cells render them less-specific for the inhibition of T cell proliferation.

In this respect, ILT3 is unique. Its expression is limited to dendritic (professional) and endothelial (semi-professional) antigen presenting cells, two cell types playing an important role in modulating the immune responses. They can be either immunogenic or tolerogenic. However, the expression of ILT3 on these two cell types renders them tolerogenic leading to induction of anergy. ILT3 can be induced with inhibitory cytokines (IL10, IFNα) and Vitamin D3 and render DC and EC tolerogenic. However, one can not ignore the possible other, as yet undiscovered effects of cytokine treatments on cells. Thus, having sILT3 directly interact with T cells, rendering them anergic, will be more effective in down-regulating the immune system.

This invention offers several advantages. First, the second polypeptide of this invention has an extended circulating half-life and provides long-term protection, acting as a long-lasting "chimeric" protein drug. The prolonged half-life permits lower dosing, thereby reducing toxicity. Second, soluble polypeptides (i.e. the extracellular domain of ILT3) and longevity-increasing polypeptides (i.e., Fc portion of Ig) useful in this invention can readily be isolated using routine methods. sILT3 can be administered subcutaneously, intradermally, intraperitoneally, or intravenously.

EXAMPLE 1

Construction of Cells Expressing ILT3 or ILT3delta

KG1 cells over-expressing human ILT3 (KG1.ILT3 cells) were generated as previously described (CC Chang et al., Nat. Immunol. 3:237-243, 2002). Deletion of the cytoplasmic region of ILT3 was accomplished by PCR amplification using the following primers: sense-5'-CCATGATATCAG-GAGACGCCATGATCCCCA-3' (SEQ ID NO: 1) and anti-sense-5'-ATGTAGCGGCCGCGTTTTCTCCCTG-GACGTCA-3' (SEQ ID NO: 2) and a plasmid containing a full-length cDNA of ILT3 (pcDNA4-ILT3) was used as template. PCR conditions were as follows: 5 min 94° C.; 30 cycles (30 sec 94° C., 1 min 68° C., 1 min 72° C.); 7 min 72° C. The PCR product was purified using a PCR purification kit (Qiagen) and subcloned into the EcoRV and NotI sites of the expression vector pcDNA4/TO/myc-His in frame with a c-myc-His epitope (Invitrogen). The resulting ILT3 deletion mutant, ILT3delta (which contains residues 1 (Met) to 328 (Asn) of human ILT3), encodes a protein that contains the putative leader peptide, the extracellular and transmembrane domains and a stretch of 48 amino acids of the cytoplasmic domain of ILT3 followed by a C-terminal myc-His tag. The ILT3delta insert was subcloned into the BglII site of retroviral vector MIG (MSCV-IRES-GFP) and the resulting construct was confirmed by sequencing. The ILT3delta was over-expressed in KG1 cells by retroviral transduction (Change et al., supra). Transfectants were sorted for GFP expression by flow cytometry.

Figure 1:
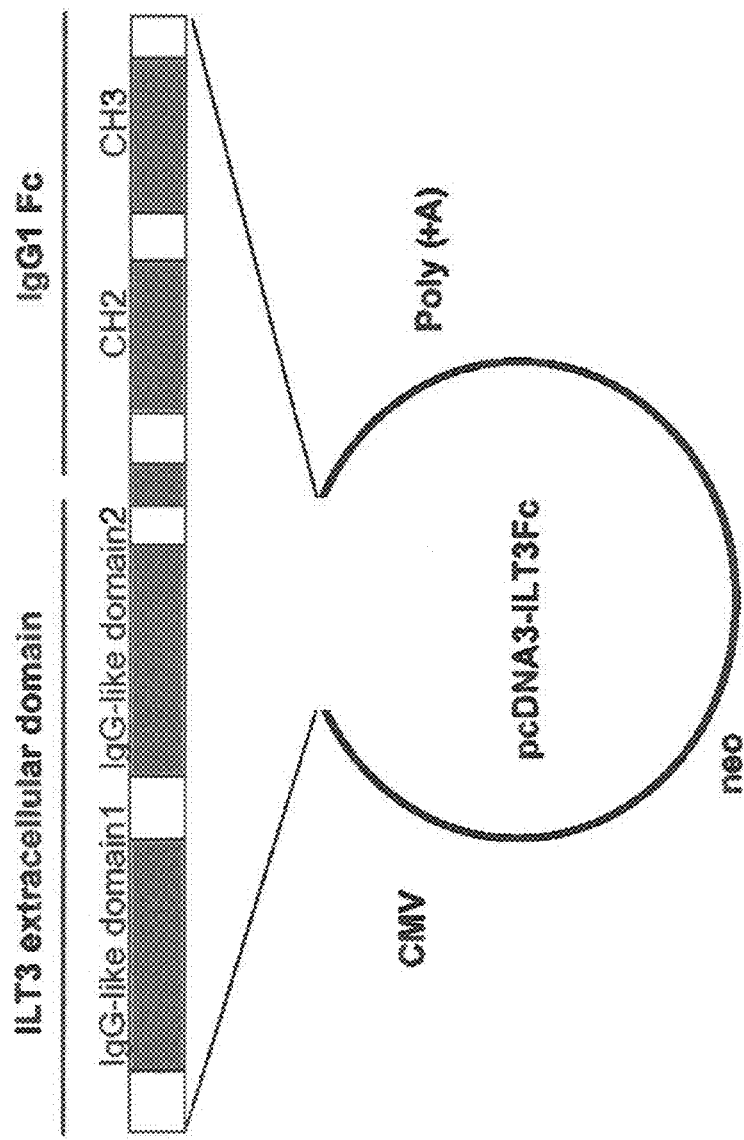
FIG. 1
Figure 2:
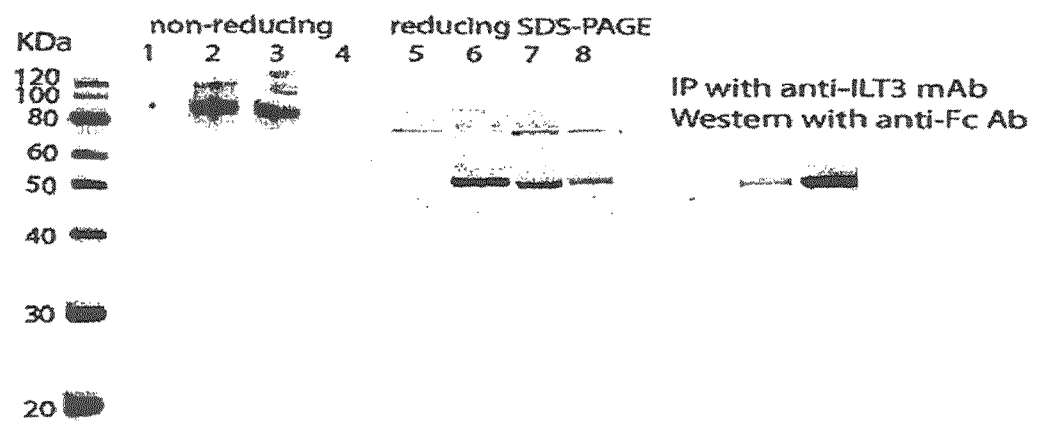

Generation of Soluble ILT3-Fc Chimeric Protein cDNA fragment coding for the extracellular domain of human ILT3 was fused to the Fc portion of the human IgG1 heavy chain. To abolish binding to the Fc receptor, a mutation was introduced in the N-linked glycosylation site, N77 (Asn>Gln) of the Fc domain. Expression vector pcDNA3 (Invitrogen) containing the ILT3-Fc fusion gene (FIG. 1) was transfected into CHO-S cells. Homogenous cell populations were obtained by limiting dilution and clones with high expression of ILT3 (as determined by RT-PCR and Western Blot analysis) were selected. ILT3-Fc fusion proteins were purified from the supernatant of the selected clones using a recombinant protein A FF column and analyzed by Western blotting using an anti-human Fc-specific antibody.

EXAMPLE 2

Figure 4A:
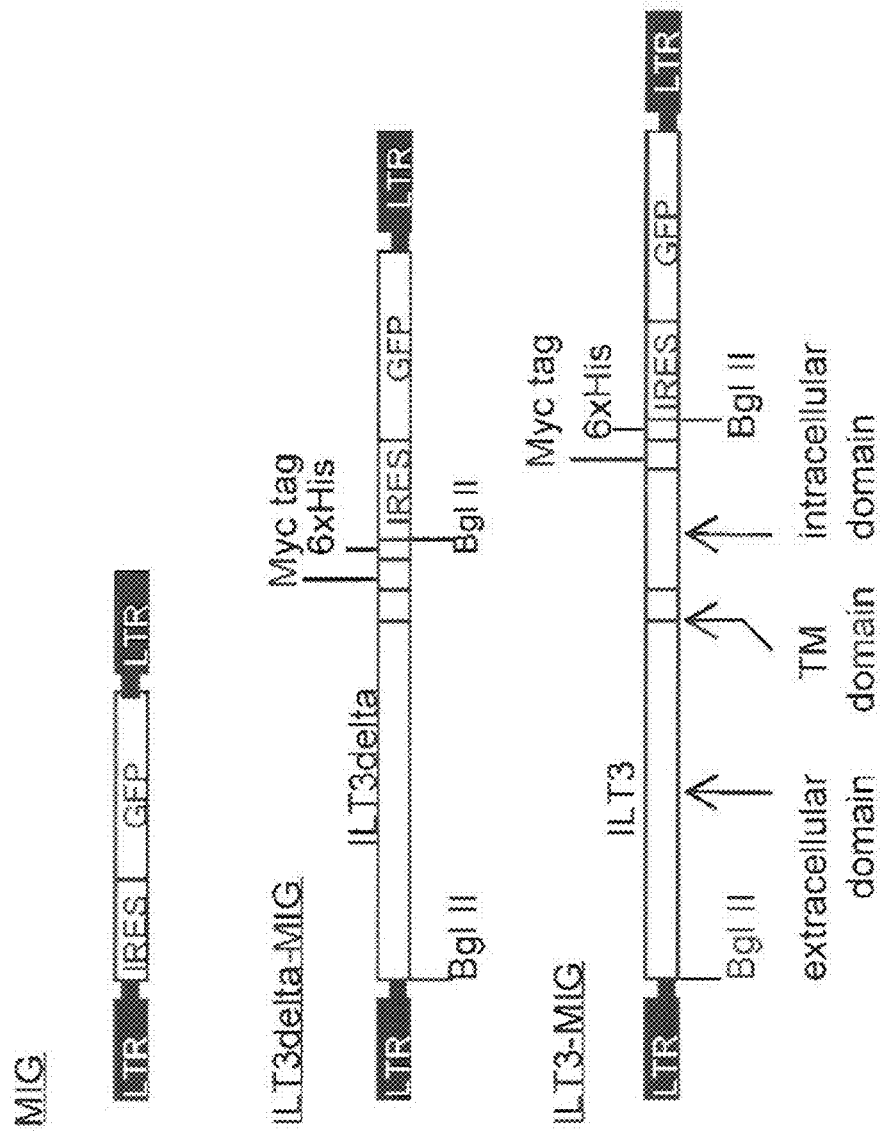

Membrane ILT3 Induces $CD4^+$ TH Cell Anergy and Inhibits the Generation of $CD8^+$ Cytotoxic Cells The cytoplasmic region of ILT3 contains ITIM motifs that recruit inhibitory phosphatases, which can negatively regulate cell activation. The extracellular portion contains two Ig domains, one or both of which are likely to contribute to the ILT3 ligand binding sites involved in the interaction of APC with T lymphocytes. By overexpressing the cytoplasmic tail deletion mutant ILT3delta in KG1 cells, we generated the KG1.ILT3delta cell line, which we then used to explore the activity of membrane ILT3 (mILT3) (FIG. 4A).

Figure 4B:
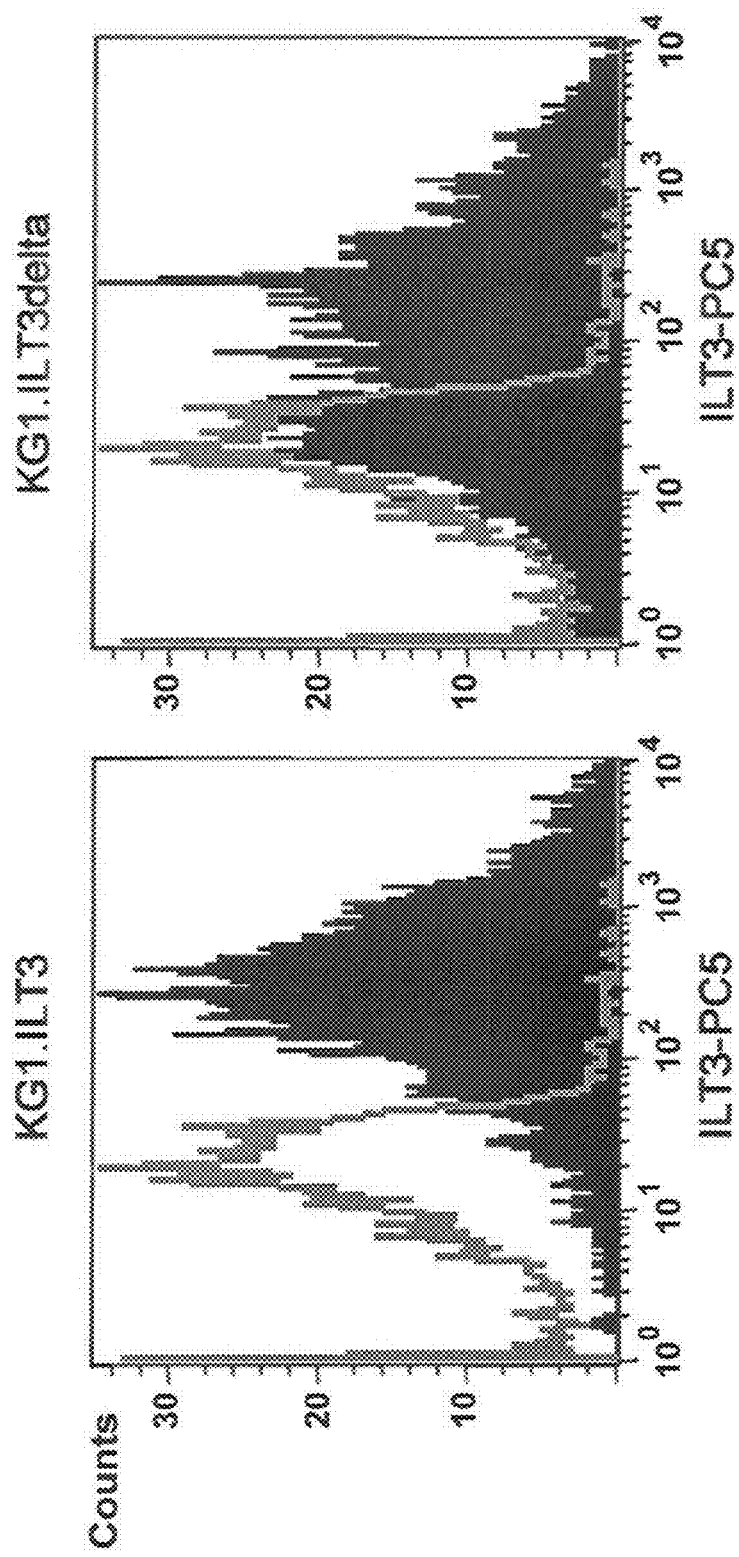
Figure 4C:
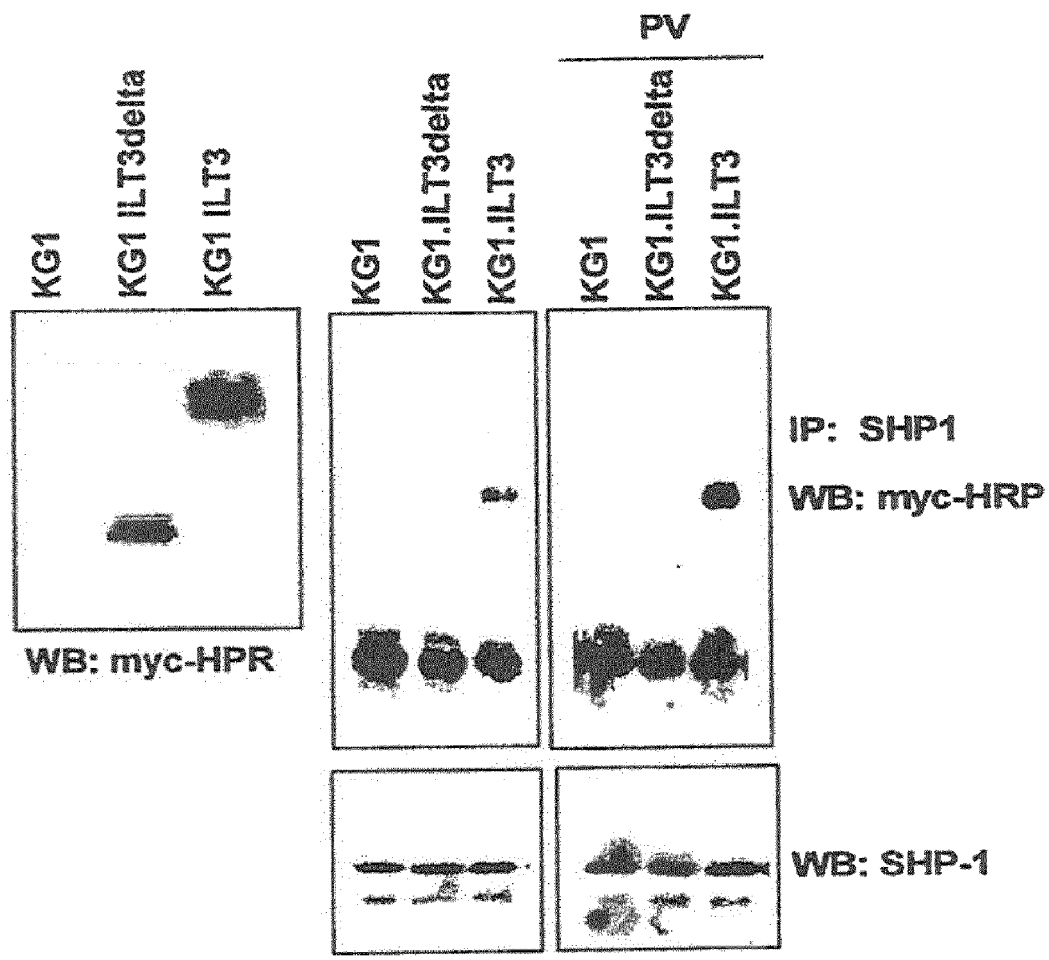

KG1.ILT3 and KG1.ILT3delta expressed similar amounts of ILT3 protein on the cell surface as shown by flow cytometry analysis using mAb to ILT3 (FIG. 4B). Western blot analysis using anti-myc antibody, which binds to the C-terminal myc tag of the recombinant proteins, demonstrated that the molecular weight of the ILT3delta protein was 38 kDa while that of full length ILT3 was 50 kDa (FIG. 4C).

ILT3 associates with SHP-1 phosphatase and this association is increased by receptor crosslinking with specific antibodies or with pervanadate treatment. SHP-1 recruitment upon phosphorylation of the cytoplasmic ITIMs has been shown to mediate the negative signaling of ILT2, a closely related member of the same family of Ig-like inhibitory receptors as ILT3. Immunoprecipitation experiments using the anti-SHP-1 antibodies and western blot analysis using an anti-myc antibody showed constitutive interaction of the full-length ILT3 molecule and SHP-1. As expected, no interaction of SHP-1 with ILT3delta was observed (FIG. 4C).

Figure 4D:
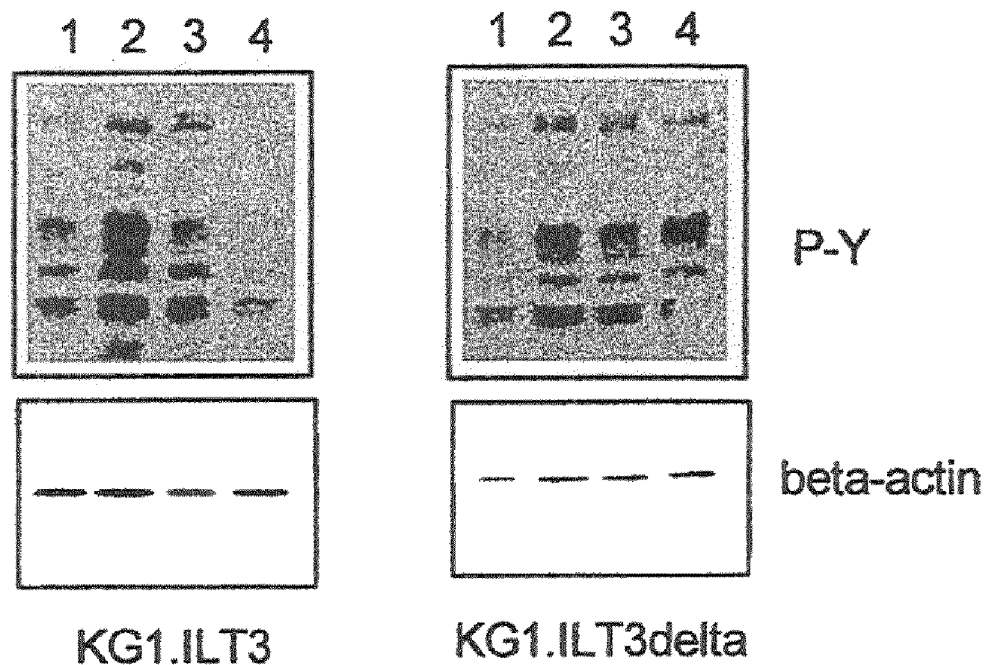

Antibodies against HLA-DR can trigger both $Ca^{2+}$ mobilization and specific protein phosphorylation. Co-crosslinking of the anti-HLA-DR antibody with anti-ILT3 antibody results in substantial inhibition or more rapid extinction of the activation signal (Cella et al., J. Exp. Med., 185:1743-1751, 1997). To establish whether lack of SHP-1 recruitment by ILT3delta was accompanied by a lack of inhibition of protein tyrosine phosphorylation, KG1.ILT3 and KG1.ILT3delta cells were ligated with anti-HLA-DR mAb or with anti-HLA-DR mAb and anti-ILT3 mAb in the presence of a crosslinking antibody. Total cell extracts were analyzed by western blot with anti-phoshotyrosine mAb and reprobed with anti-β-actin mAb for control of equal loading. The results showed that crosslinking HLA-DR and ILT3 on KG1.ILT3 cells inhibits tyrosine phosphorylation, however, it has little or no effect on tyrosine phosphorylation in KG1.ILT3delta mutants (FIG. 4D).

Comparison of the capacity of KG1, KG1.ILT3 and KG1.ILT3delta to elicit T cell proliferation in primary and secondary mixed leukocyte culture (MLC) showed that KG1.ILT3 and KG1.ILT3delta elicited much less proliferation of unprimed (FIG. 5A) or KG1-primed T cells (FIG. 5B) than KG1 cells.

For the proliferation assays, responding T cells ($5 \times 10^4$/well) were tested for reactivity to irradiated KG1, KG1.ILT3, KG1.ILT3delta, or allogeneic CD2-depleted APC ($2.5 \times 10^4$/well). After 5 days (for naive T cells) or 2 days (for primed T cells) of incubation, the cultures were pulsed with [$^3$H]-thymidine and harvested 18 hours later. [$^3$H]-thymidine incorporation was determined by scintillation spectrometry in an LKB 1250 Betaplate counter. Mean counts per minute (c.p.m.) of triplicate cultures and the standard deviation (sd) to the mean were calculated.

Addition of anti-ILT3 monoclonal antibody (5 μg/ml) or IL-2 (10 U/ml) to the blastogenesis assays restored T cell proliferation in response to KG1.ILT3 and KG1.ILT3delta (FIG. 5B). These experiments indicate that mILT3 protein is sufficient for inducing an inhibitory signal in activated T cells and that deletion of the cytoplasmic region of ILT3 does not abrogate its T cell anergizing activity.

To study the effect of ILT3 on the generation of cytotoxic T cells, $CD3^+CD25-$ T cells were primed with KG1, KG1.ILT3 or KG1.ILT3delta. After 7 days, $CD8^+$ T cells were isolated from each of the cell cultures and tested for their ability to kill KG1 cells. T cells primed with KG1.ILT3 or KG1.ILT3delta showed significantly less cytotoxic activity (6%) than T cells primed with KG1 (24%) as determined by Annexin V/Propidium Iodine staining (FIG. 5C) and produced less IFN-gamma. Thus, T cell interaction with mILT3 inhibits the differentiation of cytotoxic effector cells.

sILT3 Induces $CD4^+$ TH Cell Anergy and Inhibits the Generation of $CD8^+$ Cytotoxic Cells sILT3 expression was assayed by Western blotting. Briefly, cell extracts at equal concentration were immunoprecipitated from cleared extract using mouse anti-ILT3 mAb (ZM 3.8) and subjected to SDS-PAGE. Proteins were then electrotransferred onto polyvinylidene difluoride (PVDF) membrane, and were incubated with anti-human Fc polyclonal antibody. Immunoblots were developed by ECL and acquired by the phosphor/fluorescence imager. Apparent molecular weight of soluble ILT3 is about 90 and 50 kDA in non-reducing and reducing conditions, respectively.

Figure 6:
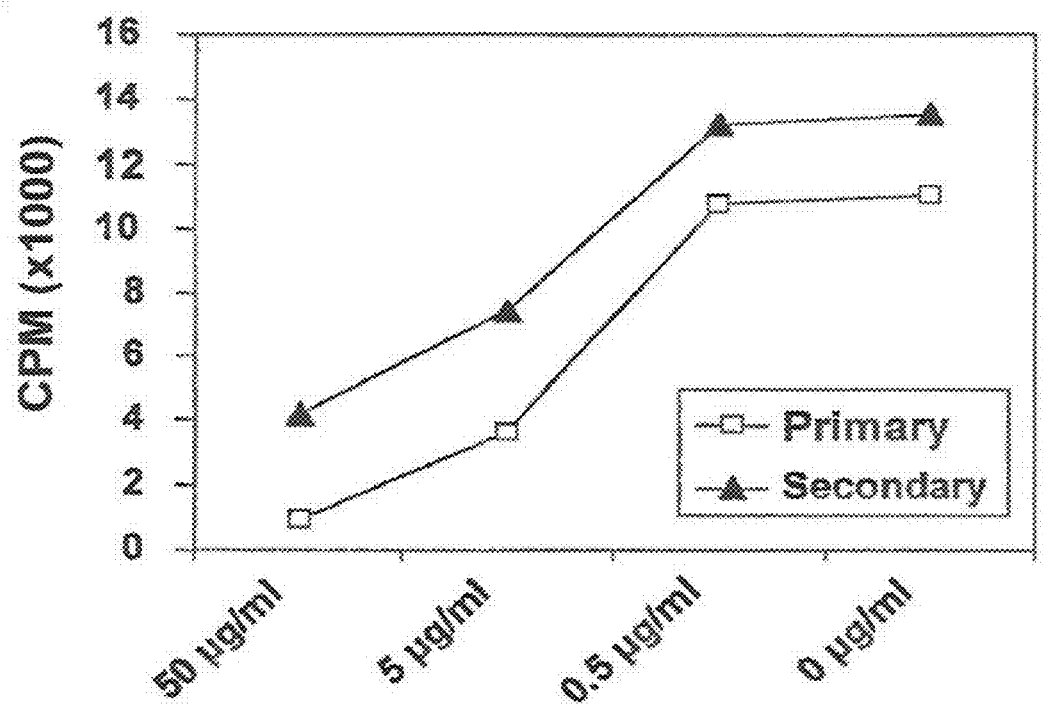

Responding $CD3^+CD25^-$ or $CD4^+CD25^-$ cells ($1 \times 10^5$ cells/well) were stimulated with irradiated KG-1 cells (30 min) ($0.5 \times 10^5$ cells/well) in the presence or absence of sILT3-Fc fusion protein in 96-well, round bottom microtiter plates. At 5 days later, cell proliferation was determined by pulsing with [$^3$H]thymidine (0.5 μCi/well) overnight and radioactivity was counted on a beta reader. Addition of 50 μg/ml sILT3 inhibited cell proliferation by >90% (FIGS. 3 and 6). Similarly, when 50 μg/ml sILT3 was added to secondary MLC at the time of restimulation there was >70% inhibition of the secondary response (FIG. 6).

Figure 7:
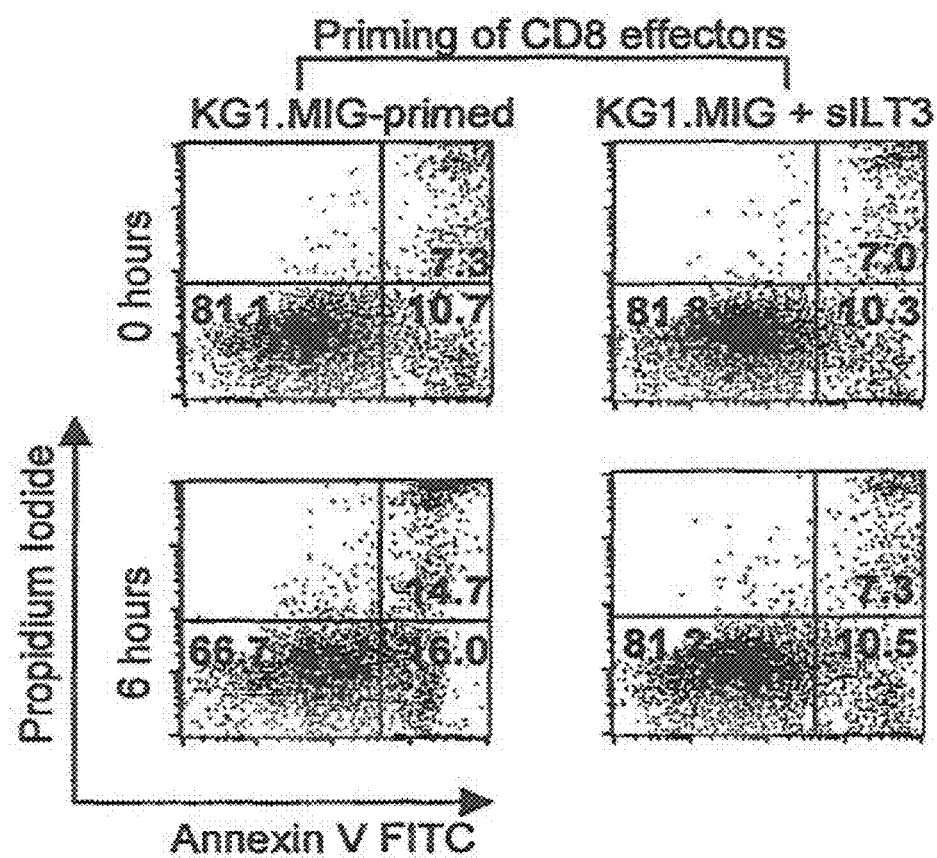
Figure 8:
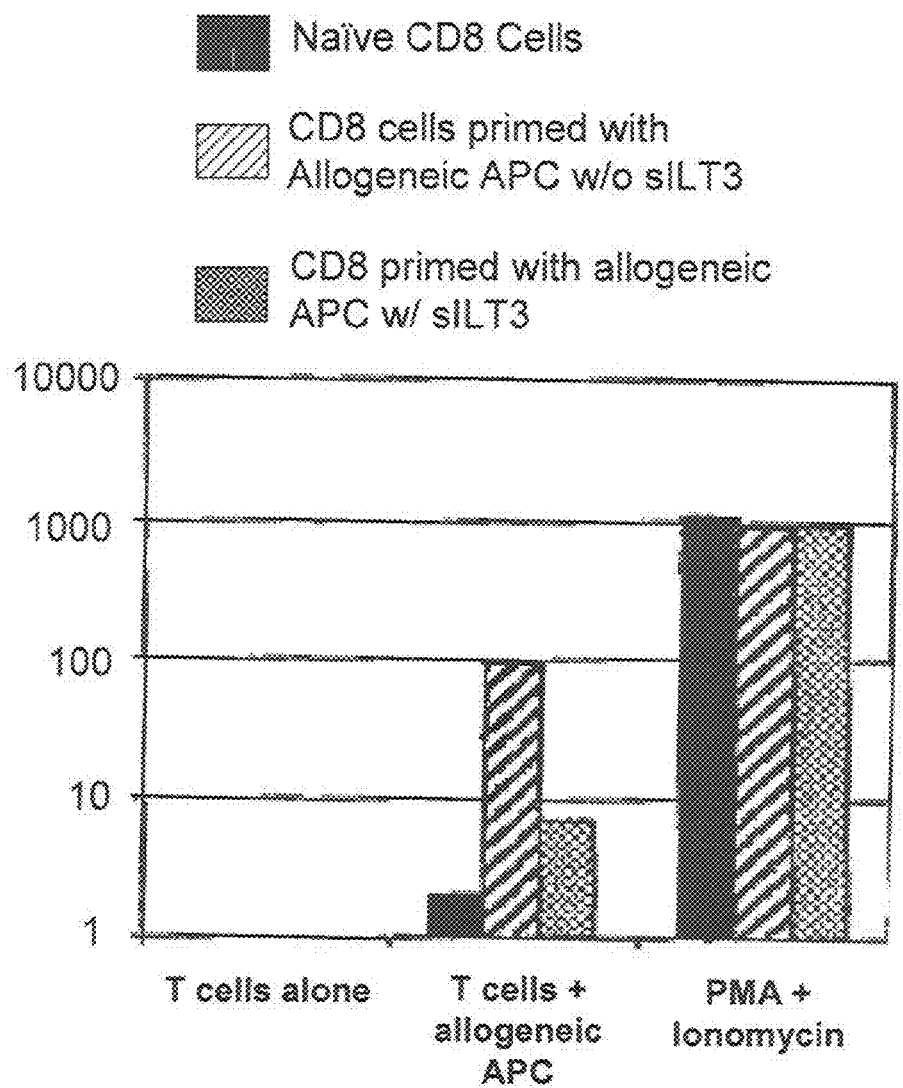

Analysis of the capacity of sILT3 to inhibit generation of cytotoxic T cells showed that $CD8^+$ T cells primed in 7-day cultures with KG1 cells, in the presence of sILT3 (50 μg/ml) were devoid of killing capacity (FIG. 7). Furthermore, $CD8^+$ T cells from these cultures did not produce IFN-gamma as demonstrated in ELISPOT assays (FIG. 8). Taken together these data indicate that sILT3, similar to mILT3, induces TH anergy and blocks the generation of cytotoxic T cells.

EXAMPLE 3 mILT3 and sILT3 Induce the Generation of Regulatory/Suppressor T Cells

The finding that sILT3 inhibits T cell proliferation in response to allogeneic stimulating cells suggested the possibility that this protein induces anergy in primed T cells triggering their differentiation into regulatory cells.

To explore this hypothesis, unprimed $CD4^+$ or $CD8^+$ T cells were incubated with allogeneic stimulators (irradiated KG1 cells) in the presence or absence of sILT3 (50 μg/ml). After 7 days, T cells were harvested from the cultures and tested for: (a) expression of FOXP3 (a T suppressor/regulatory cell marker) and (b) capacity to inhibit MLC reactions.

Figure 9A:
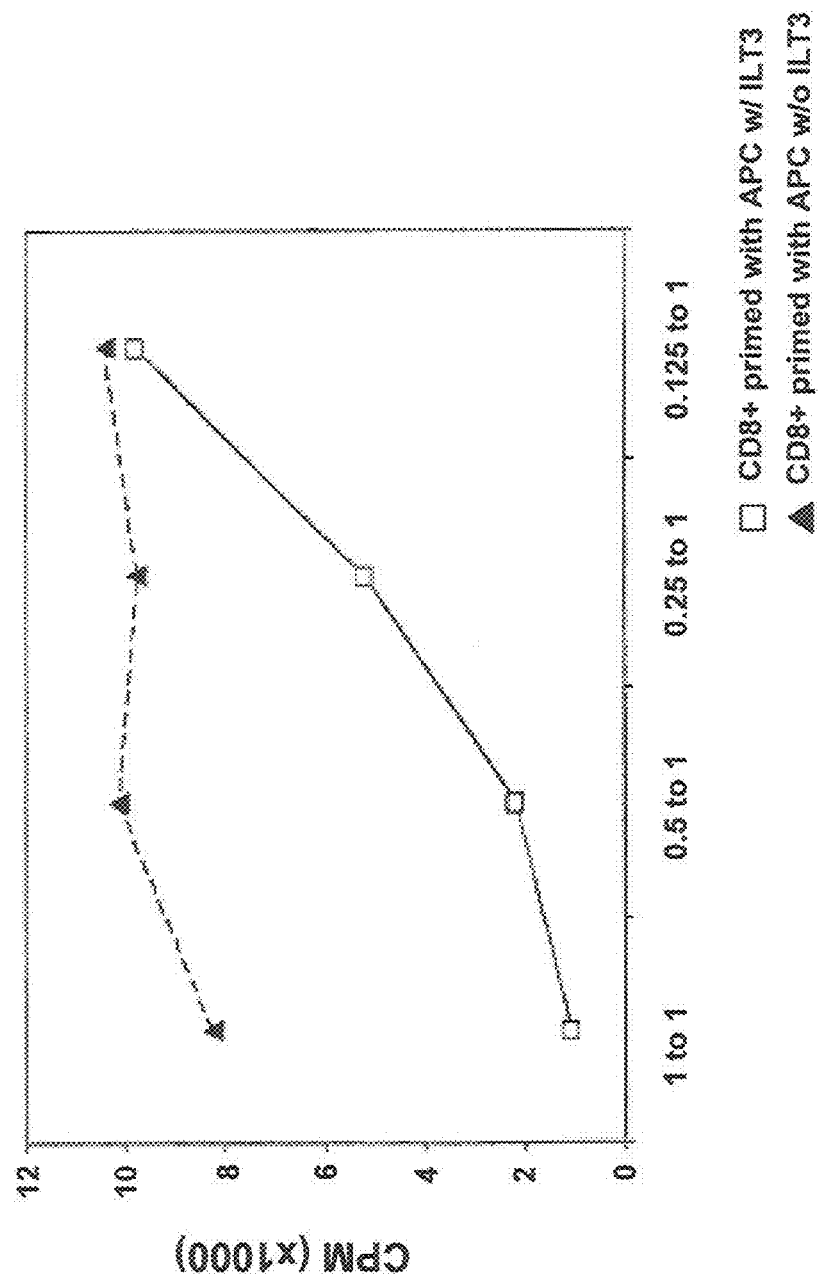

$CD4^+$ and $CD8^+$ T cells primed in the presence of sILT3 for 7 days expressed FOXP3 and suppressed KG1-triggered proliferation of naïve $CD4^+$ T cells in MLC. Control T cells primed for 7 days in cultures with sILT3 or with sILT3 but without allogeneic stimulating cells did not acquire regulatory function. $CD8^+$ T cells primed in the presence of sILT3 induced dose-dependent inhibition of T cell proliferation from 50% at a 0.25:1 ratio of primed $CD8^+$ $T_S$ to responding $CD4^+$ $T_H$ cell ratio to 90% at a 1:1 ratio (FIG. 9A). $CD8^+$ T cells primed in cultures without sILT3 induced 20% inhibition at the highest concentration and virtually no inhibition at lower doses.

Figure 9B:
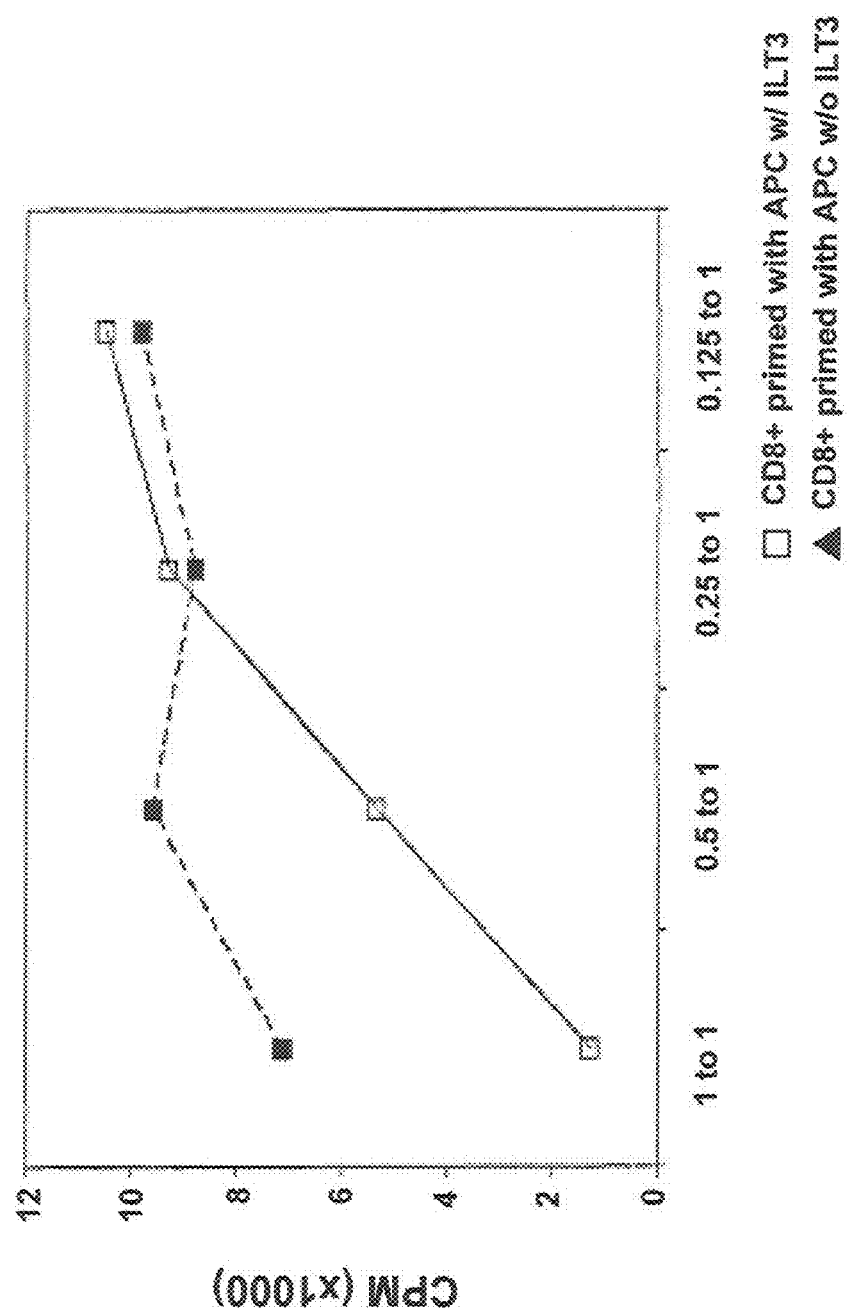
Figure 9C:
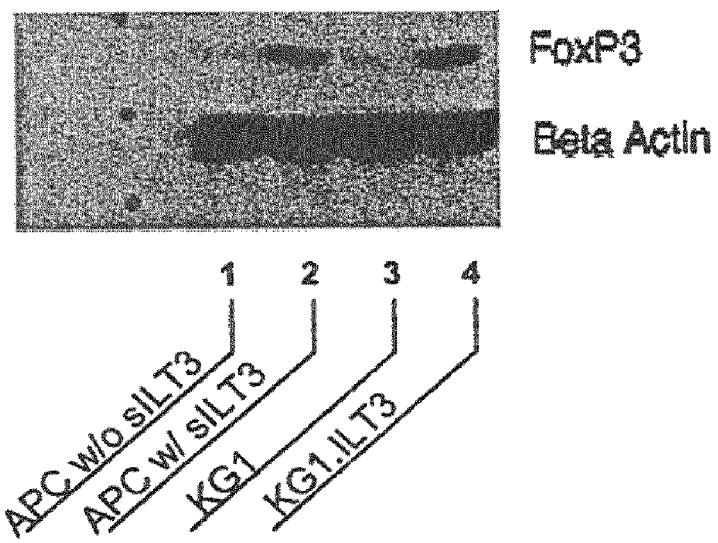

The capacity of mILT3 to induce the generation of $CD8^+$ T suppressor cells was also tested. $CD3^+CD25^-$ T cells were primed for 7 days either with KG1 or KG1-ILT3delta cells and then $CD8^+$ T cells were isolated and tested for their capacity to inhibit the response of unprimed, autologous $CD4^+$ T cells to KG1. $CD8^+$ T cells primed to KG1-ILT3 induced dose-dependent inhibition of T cell response to KG1 while $CD8^+$ T cells primed to KG1 showed inhibitory activity (35%) only at a 1:1 ratio (FIG. 9B).

Therefore sILT3 as well as mILT3 induces the differentiation of $CD8^+$ T suppressor cells in primary MLC. Since FOXP3 is a characteristic marker for $CD4^+$ and CD8+ regulatory T cells, its expression in $CD8^+$ T cells primed for 7 days to allogeneic APC in the presence or absence of sILT3 (50 μg/ml) was determined. $CD8^+$ T cells from cultures stimulated either with KG1 or with KG1.ILT3delta were also tested for FOXP3 expression. Western Blot analysis using mAb to FOXP3 (FIG. 9C) showed that both sILT3 and mILT3 induced $CD8^+$ T cells with suppressor activity and high expression of FOXP3. Taken together these data indicate that both sILT3 and mILT3 induce the differentiation of $CD8^+$ $T_S$ with potent inhibitory activity.

EXAMPLE 4 sILT3 Induces the Generation of $CD8^+$ T Suppressor Cells by Interaction with $CD4^+$ T Cells $CD8^+$ T suppressor cells generated by multiple in vitro stimulation with allogeneic APC were previously shown to act directly on APC, inducing the down regulation of costimulatory molecules and the upregulation of ILT3 and ILT4. To determine whether T suppressor cells generated by allostimulation in the presence of sILT3 have a similar effect on APC, we tested $CD8^+$ T cells primed under such conditions for their ability to modulate CD86 and ILT3 expression on DC from the donor used for priming and on control DC from an individual sharing no HLA class I antigens with the original stimulator.

Figure 9D:
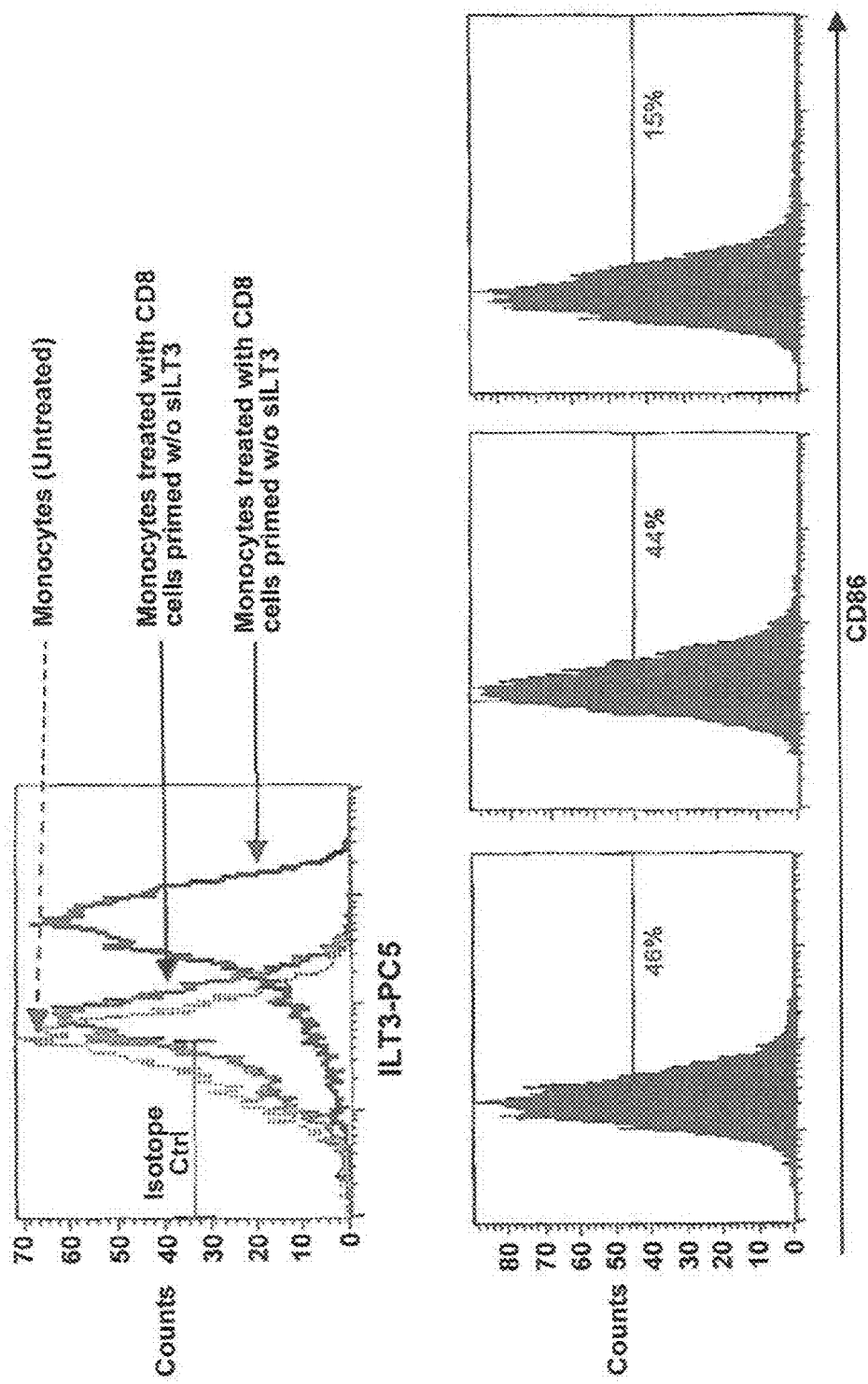

$CD8^+$ T cells isolated from the culture containing sILT3 were able to dramatically upregulate the expression of ILT3 on DC from the specific stimulator but not on control APC. This alloantigen-specific upregulation of the inhibitory receptor ILT3 occurred in conjunction with the downregulation of CD86 (FIG. 9D).

Figure 10A:
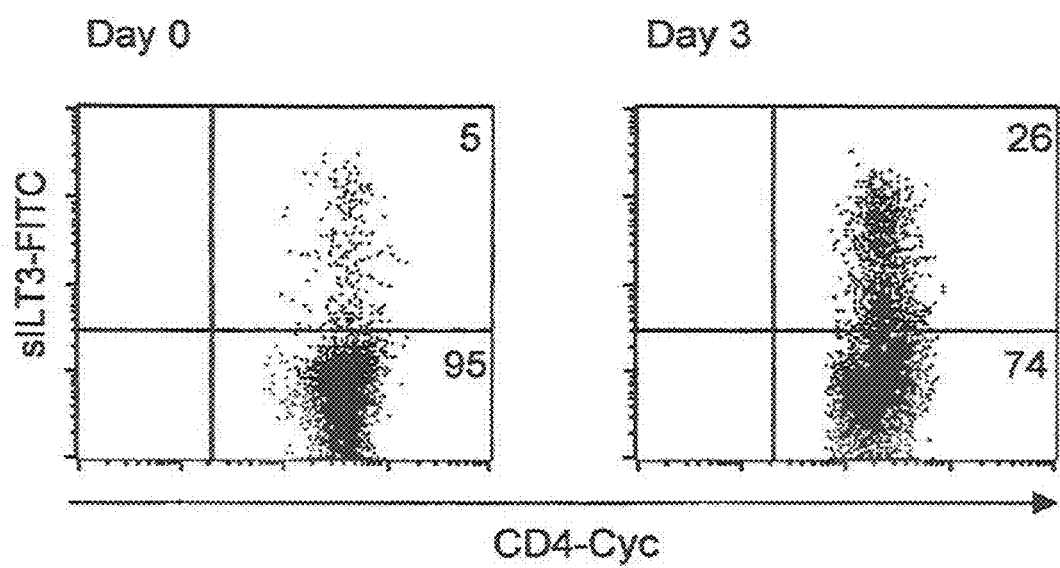
Figure 10B:
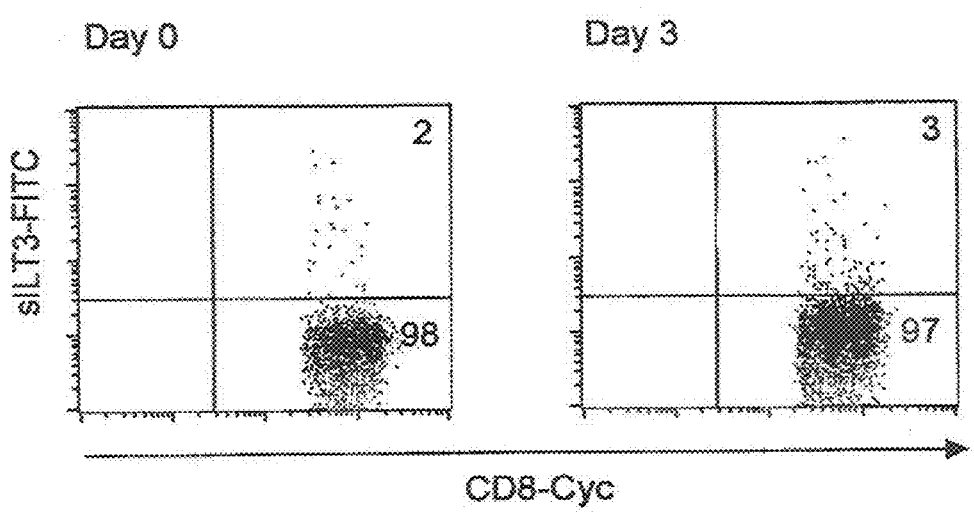

To determine if the generation of $CD8^+$ T suppressor cells is due to direct interaction of ILT3 with $CD8^+$ T cells or if it results indirectly from interaction between ILT3 and $CD4^+$ T cells, FITC-labeled sILT3 protein was used to stain T cells in primary MLC. $CD4^+$ T cells, but not $CD8^+$ T cells were stained by sILT3-FITC indicating that direct interaction of ILT3 and $CD8^+$ cells is not involved in the generation of $CD8^+$ T suppressor cells (FIG. 10).

The discovery that sILT3 has potent immunosuppressive activity and that it acts on T cells only upon activation has important clinical implication indicates that sILT3 is useful for inducing antigen specific tolerance.

sILT3 signaling in T lymphocytes via its ligand may interfere with the generation of effective immunity, promoting the generation of T cells with suppressive function. Because sILT3 has no effect on resting, non-stimulated T cells it is likely to inhibit allograft rejection mediated by T cells activated via direct or indirect pathways. Administration of sILT3 can also attenuate the proliferation of T cells involved in aggressive autoimmune responses triggered by activated DC which cross present immunogenic self-peptides. Attenuation of activation efficiency may result in stalled immune responses which perpetuate quiescence.

These findings have important clinical implications because they open two new avenues for antigen-specific suppression of the immune response in transplantation and autoimmune diseases.

The first avenue resides in treating transplant recipients at the time of or after transplantation or at the onset of an acute rejection episode with sILT3. This molecule is expected to bind only to T cells that have been activated by the transplant's alloantigens and not to unprimed T cells, thus suppressing the immune response in an antigen-specific manner. Similarly, sILT3 administration during the flare-up of an autoimmune attack, e.g., in rheumatoid arthritis, Crohn's disease, multiple sclerosis, or onset of type I JDM, may prevent the evolution, e.g., progression of the disease.

The second avenue is to use cell therapy, by leukophoresing the patient and exposing the harvested cells to sILT3 for 18 h. In vitro activated T cells, but not unprimed T cells, are expected to be converted into regulatory cells which, when reinfused into the patient, should block the progression of the immune response.

EXAMPLE 5

Islet Cell Transplantation in Humanized NOD/SCID Mice

Although many biological mechanisms are similar in rodents and humans, there are several structural and functional differences which can render the extrapolation of experimental results to clinical practice difficult. Thus, humanized mice, defined as immunodeficient mice engrafted with human haematopoietic stem cells or PBMC, provide a powerful and productive tool for preclinical testing of new immunomodulatory agents and study of human immune responses. This is particularly true in the case of ILT3 which, like other members of the Immunoglobulin Gene Superfamily, has no ortholog in rodents.

To demonstrate that sILT3 prolongs islet allograft survival we used the humanized Non-Obese Diabetic/Severe Combined Immunodeficiency (hu-NOD/SCID) mouse model developed by Gregori et al. NOD mice are used as an animal model for type 1 diabetes. SCID mice present without the ability to make T or B lymphocytes. As such, the mice cannot fight infections and are also unable to reject tumors or transplants. NOD/SCID mice (N=89) were rendered diabetic by a single injection of streptozotocin (STZ; Sigma-Aldrich) at a dose of 180 mg/kg. STZ-toxicity caused the death of 33% of the injected animals (29/89) within 72 hours. Blood glucose levels of the surviving mice were measured twice a week using Ascensia Elite XL Blood Glucose Meter system (Bayer AG). Diagnosis of diabetes was based on two consecutive glucose measurements>350 mg/dl. All but 8 of the remaining 60 animals (87%) became diabetic 3-6 days after STZ injection.

The diabetic animals were then transplanted with 1500 IEQs (islet equivalent) of human islets, via injection under the kidney capsule as described in Davalli et al. (1996, Diabetes, 45:1161-1167; fully incorporated herein by reference). Purified human pancreatic islets from human were obtained from the National Islet Cell Resource Center Program. The islets were cultured in CMRL1066 culture medium supplemented with 10% FCS, 2 mM L-glutamine, 100 U/ml penicillin, and 100 mg/ml streptomycin at 37° C. in a 5% $CO_2$, humidified atmosphere. All islet samples were >70% pure and 90% viable. Purity was determined by the percentage of dithizone-positive particles, and viability was determined by fluorescein diacetate and propidium iodine staining.

Following islet cell transplantation, mice that did not achieve euglycemia (glucose level<100 mg/dl) were eliminated from the study on the assumption that the grafted islets were not functional (Some animals died 48 hrs post-operation and others received islet cells that were non-functioning and failed to recover from the STZ-induced diabetes). Out of the fifty-two animals, thirty-two were successfully transplanted, as they became euglycemic within 7 days.

7 to 10 days post-transplantation, mice that were restored to euglycemia were humanized. That is, they received an intraperitoneal (i.p.) injection of $50 \times 10^6$ freshly isolated peripheral blood mononuclear cells (PBMC) from healthy human blood donors, isolated from fresh buffy coats purchased from the New York Blood Center. These PBMC then develop into functioning T-cells, restoring immune function to the immunodeficient mice.

Ten days after PBMC injection, circulating human T cells (which developed from the injected PBMC) taken from heparizined retro-orbital venous samples were evaluated by flow cytometry. Animals that failed to be reconstituted with human T cells were excluded from further analysis by prior design. To avoid variability between samples, both islets and PBMC were administered to mice from the sILT3 and human IgG group in a pairwise fashion.

Immunomodulatory Effect of ILT3-Fc in islet cell Transplantation in Diabetic Hu-NOD/SCID Mice Concurrently with the PBMC injection, the mice were begun on a treatment regimen. The mice were assigned to one of three groups: 1) the treatment group, which received a daily intraperitoneal injection of 250 µg sILT3, for ten consecutive days 2) the IgG control group, which received 250 µg human IgG instead, and 3) the no-treatment control group, which received no treatment.

Figure 11:
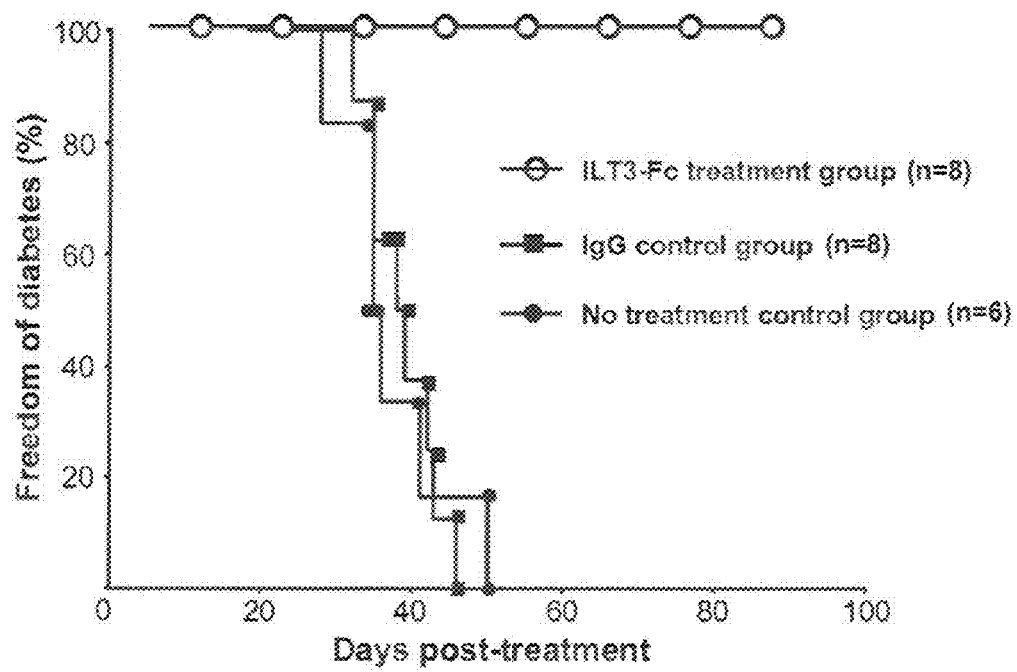

Blood glucose levels were measured twice a week before, during, and after the treatment period in order to assess the health of the islet cell graft. Within the group of IgG-treated control animals (N=16), eight rejected the graft within 3 to 7 weeks. Those mice again became diabetic, demonstrated by the increase in blood glucose above 350 mg/dl, as well as by histological studies (described below). Similar results were seen in the no-treatment control group. By contrast, none of the ILT3-Fc treated hu-NOD/SCID mice became diabetic over 91 days of observation (Table 1 and FIG. 11). Animals that developed graft versus host disease (hunched back, lethargy, weight loss, and tachypnea) were excluded from the analysis of rescue from diabetes. Actuarial freedom from diabetes was 100% in the ILT3-Fc treatment group, indicating that soluble ILT3 (sILT3) inhibited rejection of islet allografts in all hu-NOD/SCID recipients (p=0.0001) (FIG. 11).

Using ILT3-Fc treatment, we prevented rejection of islet grafts in 100% of hu-NOD/SCID recipients. To our knowledge this is the highest rate of successful transplantation of allogeneic human islets in a pre-clinical model in which the efficacy of a biological agent was tested alone, without any complementary pharmaceutical immuno-suppression.

TABLE 1

Blood glucose levels in hu-NOD/SCID islet allograft recipients treated with ILT3-Fc or control human IgG.

| Week | Control group | | Treatment group | | P-value |
|---|---|---|---|---|---|
| Week #1 | n = 16 | 84.4 ± 31.1 | n = 16 | 79.3 ± 10.4 | N.S. |
| Week #2 | n = 16 | 80.1 ± 22.0 | n = 16 | 77.3 ± 9.4 | N.S. |
| Week #3 | n = 16 | 103.7 ± 55.4 | n = 16 | 74.9 ± 9.0 | P = 0.057 |
| Week #4 | n = 13 | 104.1 ± 30.2 | n = 15 | 76.6 ± 11.9 | P = 0.008 |
| Week #5 | n = 12 | 197.3 ± 103.9 | n = 13 | 73.6 ± 8.6 | P = 0.002 |
| Week #6 | n = 8 | 237.8 ± 122.7 | n = 12 | 78.8 ± 10.3 | P = 0.0008 |
| Week #7* | n = 4 | 279.8 ± 91.9 | n = 12 | 81.9 ± 22.2 | P = 0.02 |

*Due to attrition in the control group, no statistical comparison can be performed after week 7.

EXAMPLE 6

In Vivo Generation of Regulatory and Suppressor T Cells in ILT3-Fc Treated Animals We further demonstrated that the human PBMC injected into the hu-NOD/SCID mice differentiate into regulatory T cells in vivo, and that the administration of ILT3-FC to the host favored the differentiation of PBMC into T cells with immuno-suppressive activity, e.g., $CD8^+$ suppressor T (Ts) cells. Four hu-NOD/SCID mice, prepared in the same way as those described above, were transplanted with islets from a human donor expressing HLA-A1, B8, DR3/A2, B44, and DR7. Two mice were treated with ILT3-Fc, and the other two were treated with IgG. One from each pair was sacrificed on day 23 after human PBMC injection, when glycemia was 240 mg/dl (signaling the onset of transplant rejection and relapse of diabetes) in the IgG-treated mouse and 72 mg/dl (normal glycemic levels) in the ILT3-Fc treated mouse. The remaining two were sacrificed on day 47. At the time of sacrifice at day 47, the IgG-treated mouse had a diabetic blood glucose level of 380 mg/dl and the ILT3-Fc-treated mouse had a euglycemic blood glucose level of 80 mg/dl.

Human CD8+ and CD4+ T cells were magnetically sorted from the spleen of the hu-NOD/SCID mouse recipients (using isolation kits by StemCell Technologies). These sorted CD4+ or CD8+ T-cells were added at increasing numbers (1-8×10$^4$/well) to a fixed number (10$^4$/well) of unprimed autologous CD3+CD25− T-cells (used as responders) and stimulated for 6 days in mixed leukocyte culture (MLC) with irradiated, allogeneic PBMC sharing HLA-A, -B, and -DR antigens with the islet transplant donor. The cultures were harvested after 6 days, and [3H]thymidine incorporation was measured to assay T cell reactivity.

Figure 13:
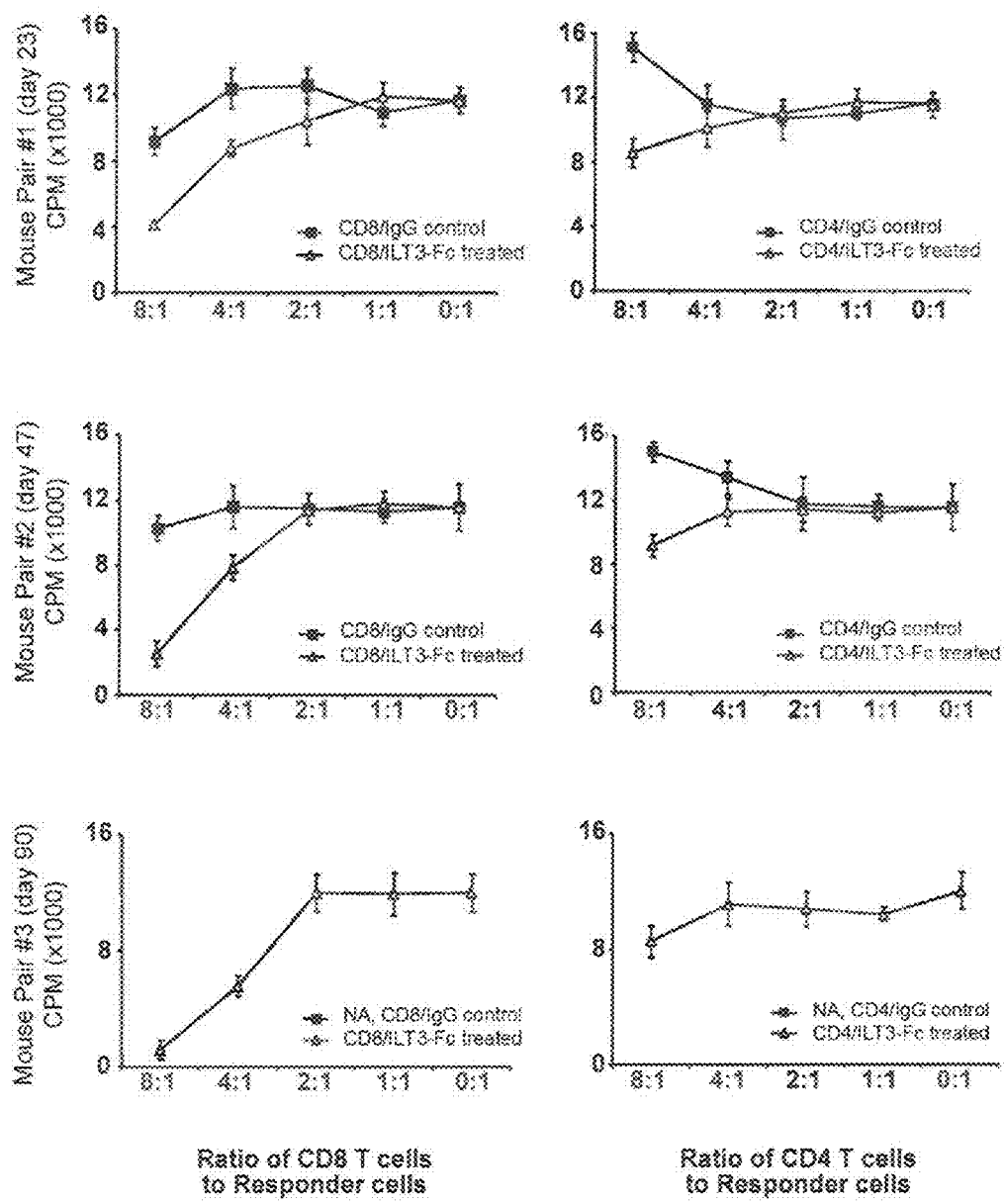

CD8+ T cells obtained from the ILT3-Fc treated mice sacrificed on both days 23 and 47 (after PBMC injection) suppressed T cell reactivity, confirming their identity as $T_S$ cells (FIG. 13). For example, CD8+ T cells isolated on day 47 from ILT3-Fc-treated mice suppressed the reactivity of responder T cells by 78% when cultured at an 8:1 ratio of regulatory to responder T cells (FIG. 13, Mouse pair #2, left graph). At this ratio (of 8:1), CD4+ T cells isolated from these ILT3-Fc treated animals also had suppressive activity, and suppressed T cell activation by 21% (FIG. 13, Mouse pair #2, right graph). By contrast, T cells generated from injected human PBMC in the control mice (IgG-treated, lacking ILT3 treatment) did not become $T_S$ cells. CD8+ T cells isolated from the control mice (IgG-treated) lacked immunosuppressive activity, and CD4+ T cells isolated from the control animals even had a mild immuno-activatory effect (mouse pairs #1 and #2, right graphs). Therefore, the administration of LIT3-Fc facilitated immunosuppression by facilitating the production of CD8+ $T_S$ cells, as well as CD4+ T cells with immunosuppressive activity.

To show that the presence of CD8+ $T_S$ cells is associated with tolerance to the allogeneic islet transplants, we tested CD8+ and CD4+ T cells isolated from the spleens of ILT3-Fc-treated euglycemic hu-NOD/SCID mice sacrificed on day 91. Antigen-presenting cells (APCs) sharing HLA-class I and class II antigens with the islet graft were used for stimulating T cells autologous to the cells tested for suppressive activity. As illustrated in FIG. 13 (Row three—Tolerant Mouse), human CD8+ T cells isolated from mice with long lasting tolerance (N=8) displayed suppressive activity. CD4+ T cells from the same animals also showed weak suppressive activity (<20%). Therefore, the data demonstrate that administering ILT3-Fc to the host prevents islet allograft rejection, and does so by inducing the formation of regulatory T cells, e.g., CD8+ $T_S$ cells and CD4+ T cells with immunosuppressive activity.

Figure 14A:
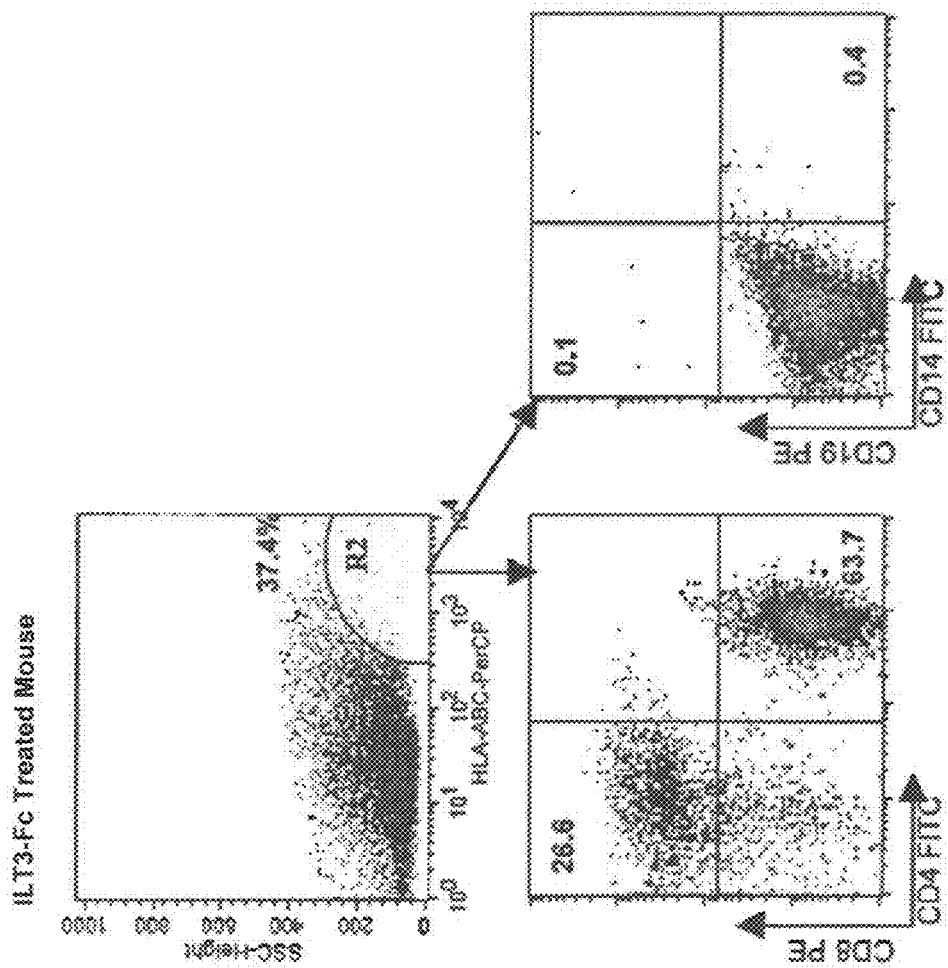
Figure 14B:
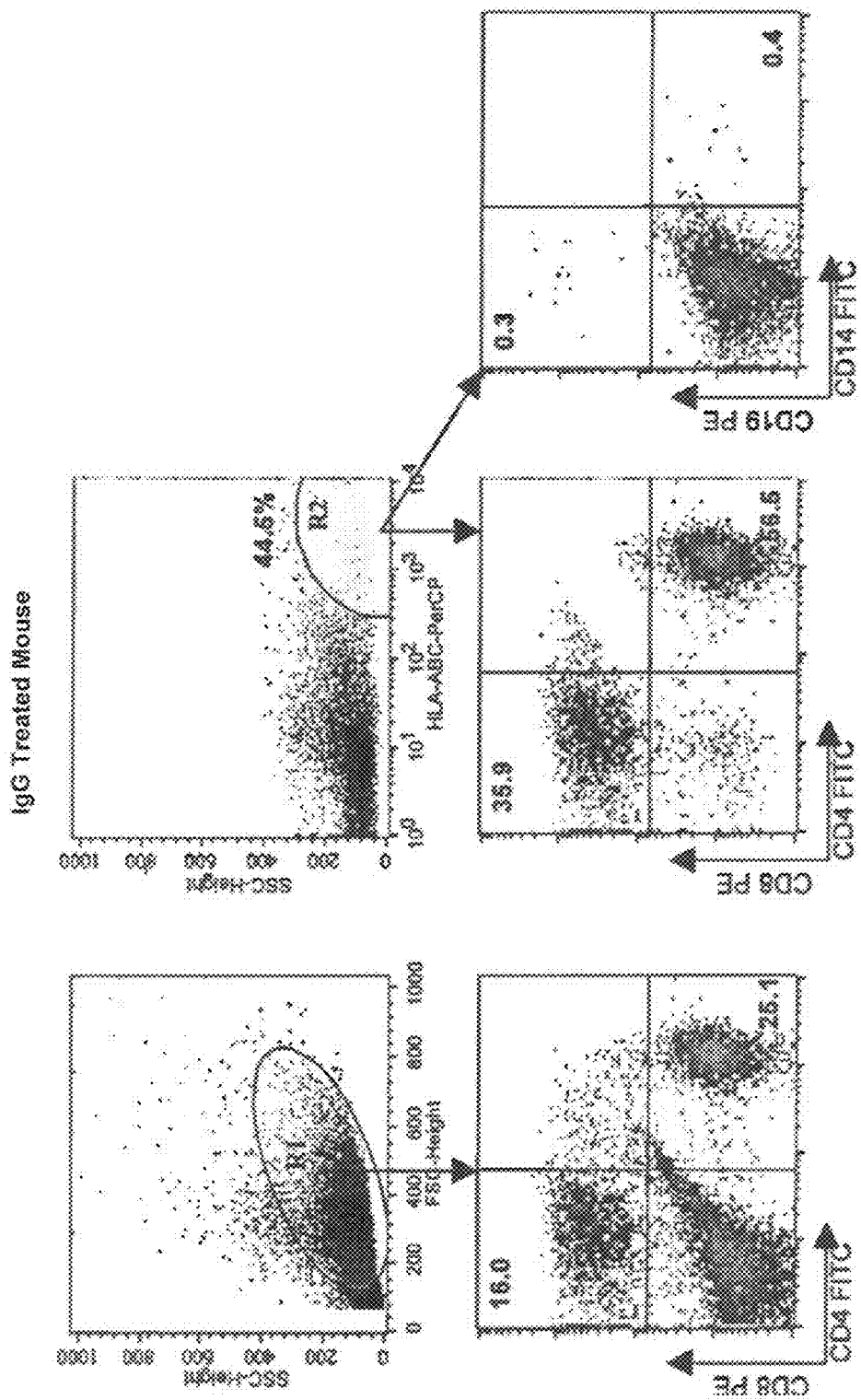

Overall engraftment of human T cells into recipients' spleens was unaffected by ILT3-Fc administration, and the distribution of CD4+ and CD8+ cells, as well as CD14+ and CD19+ cells, was similar between the ILT3-Fc and human IgG-treated mice, as illustrated in FIG. 14. These experiments served as valuable controls, and demonstrated that administration of ILT3-Fc into the host reduced allogeneic transplant rejection through inducing the differentiation of transplanted PBMC into regulatory T cells, e.g., CD8+ suppressor T ($T_S$) cells, rather than through a non-specific effect such as reduced overall engraftment of PBMC.

The Effect of sILT3 Administration on Gene Expression in Engrafted Human T Cells To further characterize the phenotype and function of effector and $T_S$ cells present in the transplant recipient mice, we performed real time PCR studies to assay the expression of inflammatory cytokines by human CD4+ and CD8+ cells sorted from the spleens of these mice sacrificed on days 23 and 47 (after humanization). Total RNA was isolated with the RNAqueous-4PCR kit (Stratagene, La Jolla, Calif.). Complementary cDNA was synthesized using the 1st Strand cDNA Synthesis Kit for RT-PCR (Roche Diagnostics, Basel, Switzerland). Real-time PCR was performed using Taqman gene expression primer probes (Applied Biosystems, Foster City, Calif.). Data were collected and analyzed with the 7300 SDS 1.3.1 software (Applied Biosystems). The relative amount of gene expression was calculated by the formula: $2^{-\Delta Ct}$, where $\Delta Ct=[Ct(gene)-Ct(glyceraldehyde-3-phosphate\ dehydrogenase)]$ and Ct is the "crossing threshold" value returned by the PCR instrument for every gene amplification. We found that treatment with ILT3-Fc inhibited the capacity of both CD4+ and CD8+ T-cells to produce Th1-type (IFN-γ and IL-2) and Th2-type (IL-5 and IL-10) cytokines (FIG. 15A). We also assayed the expression of T-cell activation markers CD28 and CD40L by human CD8+ T-cells colonizing the spleens using flow cytometry. Flow-cytometry studies were performed on a FACSCalibur instrument using six-parameter acquisition (BD Biosciences). The frequency of CD8+CD28+ T-cells was significantly lower on weeks 4 and 7 (P=0.011 and 0.048) in ILT3-Fc-treated animals compared with paired controls as illustrated in FIG. 15B. Similarly, the frequency of CD8+CD40L+ was significantly lower (P=0.007 and 0.022) in ILT3-Fc-treated animals compared with paired controls (see FIG. 15B). This down-regulation of CD28 expression in CD8+ T cells from animals treated with ILT3-Fc corroborates our, and other investigators' previous, findings that CD8+ $T_S$ cells characteristically have low expression of CD28. In addition, the CD40-CD40L costimulatory pathway is deemed to be crucial to the activation and differentiation of T effector cells. Because CD40 is expressed by pancreatic islet cells, a down-regulation of CD40L also corroborates the immunosuppressive action of ILT-3 administration.

These results demonstrate that primed CD8+ T-cells from ILT3-Fc-treated animals differentiate into $T_S$ cells, which have a significantly reduced capacity of producing inflammatory cytokines and have low CD28 and CD40L expression, and are thus unable to trigger danger signals from the islet transplant, resulting in the prevention of transplant rejection.

EXAMPLE 7

Histology: Detection of Transplant Rejection and Graft Versus Host Disease (GVHD)

Islet-engrafted kidneys from humanized NOD/SCID mice (treated with ILT3-Fc or IgG) were dissected out and twenty serial paraffin sections of were cut at 4-μm thickness. Levels 1, 10, and 20 were stained for light microscopic evaluation (hematoxylin-eosin). The remaining sections were used for immunostains including stains for insulin, CD4 (Biogenics, San Ramon, Calif.), CD3 and CD8 (Dako, Carpinteria, Calif.), and CD40 (Abcam, Cambridge, Mass.). Islet quantity and islet lymphocytic infiltration (insulitis) were graded semi-quantitatively in blinded fashion by a renal pathologist on a scale of 0 to 3+. The degree of infiltration by CD8+ T-cells into the islets was graded according to the number of CD8+ cells per ×40 high-power field: 0 (none), 1+ (1-10), 2+ (11-25), and 3+ (>25). The results were averaged over at least five high-power fields per slide.

Comparison of immuno-stained sections of islet-transplanted kidneys 23 days after human PBMC administration (i.e. 30 days post-islet transplantation) showed that islet quantity was greater in the ILT3-Fc-treated animal (3+) than human IgG treated control (2+) animal (FIG. 17A-D). In addition, there was insulitis by CD8+ T lymphocytes in the control mouse but not in the ILT3-Fc-treated mouse (2+ vs. 0.5+. respectively; FIGS. 17E and F).

Figure 19:
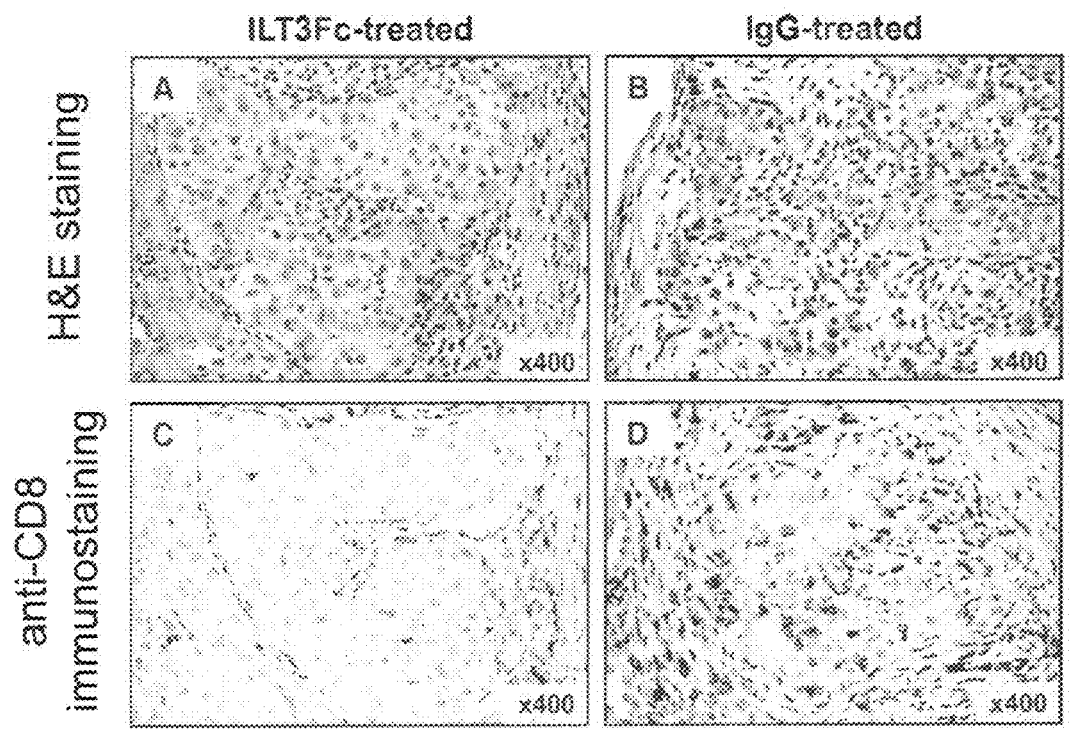

Pairwise comparison on day 47 showed that islet quantity was greater in ILT3-Fc-treated (mean score of 3+) compared to control (mean score of 1+) mice (FIGS. 19A and B). In addition, slices immunostained with anti-insulin antibodies showed marked reduction of insulin expression by islet β-cells from the IgG treated mouse, indicating transplant rejection (FIGS. 20B and D), compared with strong and widespread expression in the ILT3-Fc-treated animal (FIGS. 20A and C), indicating that the islet transplants were functionally active and well-tolerated. Insulitis by CD8$^+$ cells was markedly lower in ILT3-Fc-treated (mean score 0.5+) vs. IgG-treated control (mean score 2.5+) mice (FIGS. 19 C and D). By light microscopy, islets with insulitis from control animals exhibited scattered apoptotic bodies.

Figure 20:
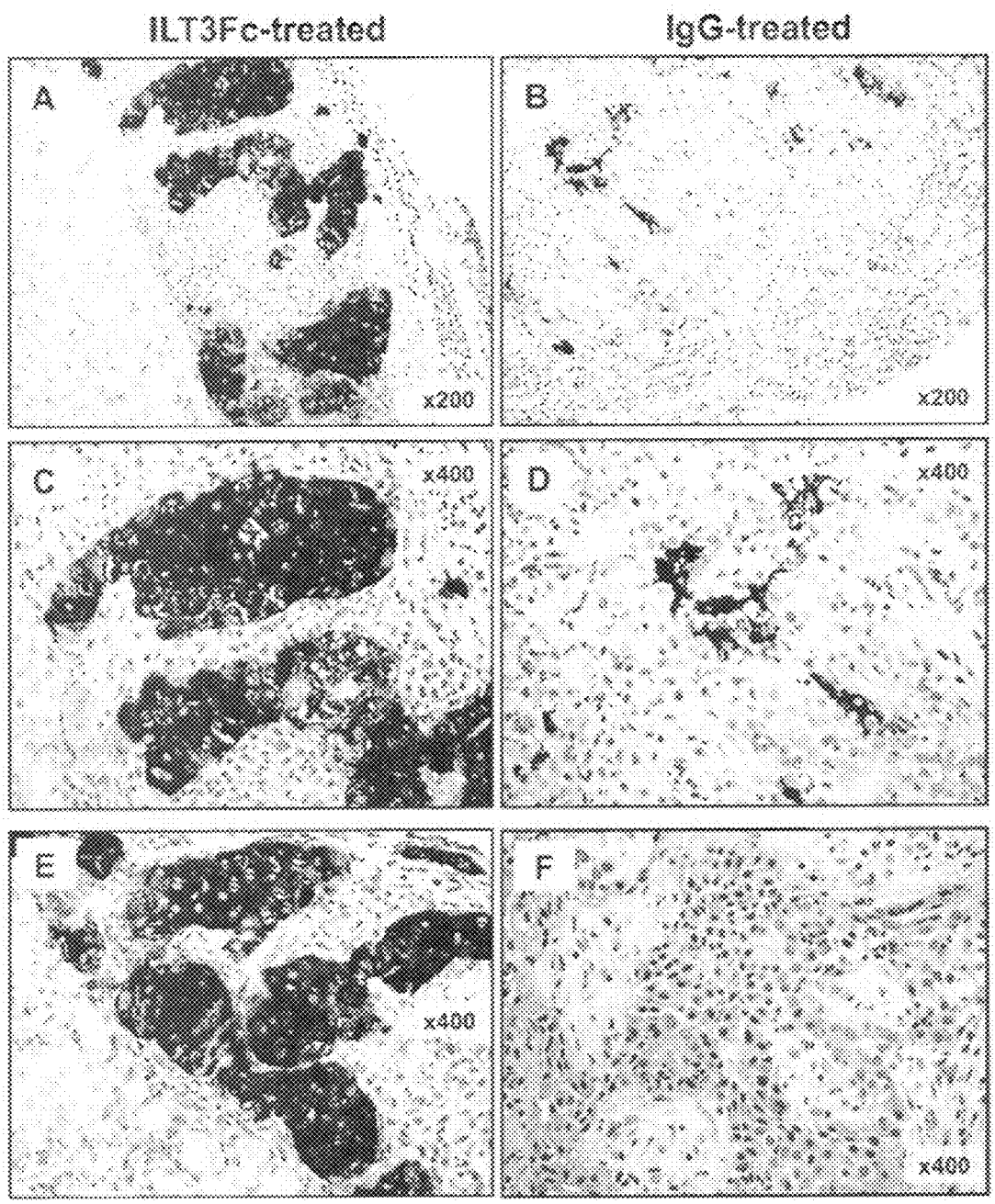

At 3 months, the tolerated islets in ILT3-Fc-treated mice displayed strong and diffuse staining for insulin, indicating that the islets were functionally active and well tolerated (FIG. 20E). Further, there was a large quantity of islets (3+) and no insulitis (0; FIG. 20F), demonstrating that the graft was well tolerated.

These histological findings confirm that the IgG-treated host was undergoing islet allograft rejection, and that administration of ILT3 was able to suppress transplant rejection.

Prevention and Treatment of GVHD

Successful engraftment of human PBMC in SCID mice has been known to result in the development of GVHD, where the implanted T cells mount an immune response against the host, resulting in T-cell expansion and tissue destruction (Hoffmann-Fezer et al., 1993). Animals developing GVHD display symptoms such as hunched back, lethargy, weight loss and tachypnea. We found that over time, a portion of hu-NOD/SCID mice (whether they were treated with ILT3-Fc or IgG) developed these symptoms and subsequently died, even in mice that maintained viable islet grafts and euglycemic blood glucose levels.

Histological studies confirmed that these mice developed GVHD. Although inflammation near the islet graft site can result from transplant rejection, the mice showing signs of GVHD developed inflammation in areas unconnected to the transplantation site. We observed perivascular inflammation in the kidney contralateral to the one receiving the implanted islet cells, perivascular and peripelvic inflammation of kidney tissue distant from the implanted islet cells, and peri-bronchial and peri-vascular inflammation in the lungs.

Figure 18:
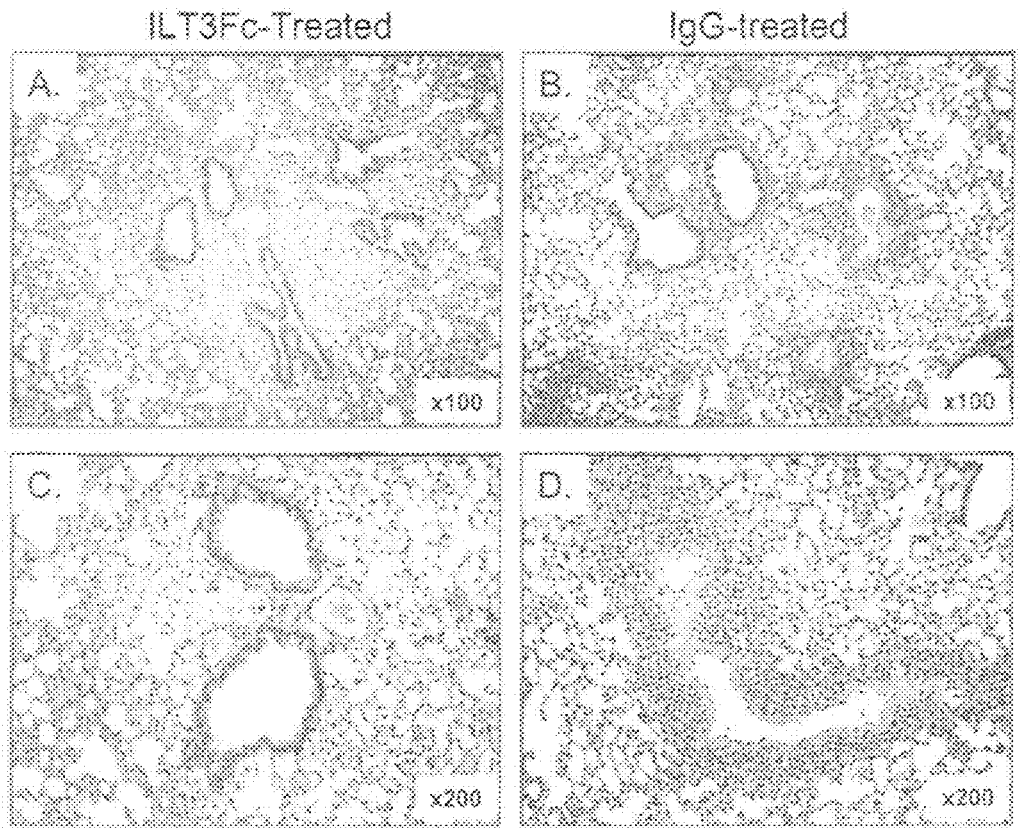

Comparison of the histological sections between a ILT3-Fc and a IgG (control) treated mouse demonstrated that the GVHD-related symptoms were less severe in ILT3-Fc treated mouse. Perivascular inflammation was identified in the control animal, but was not found in the ILT3-Fc treated animal (2+ vs. 0). In the IgG-treated mouse, the Perivascular inflammation involved both the kidney that received islet cell implants (FIGS. 17C and D) and the contralateral kidney that did not receive implants. Examination of hematoxylin and eosin (H&E) stained sections of the lungs showed diffuse peri-bronchial and peri-vascular inflammation in the IgG treated animal (FIGS. 18B and D) while lung sections from the ILT3-Fc treated animal appeared normal (FIGS. 18A and C). In addition, control mice had more pronounced perivascular and peripelvic inflammation of kidney tissue distant from the islets, with scores ranging from 0-2+ in the ILT3-Fc treated group to 3+ in the IgG-treated group.

Our results showing that ILT3-Fc treatment suppressed GVHD-specific conditions demonstrate that ILT3-Fc treatment inhibited not only the onset and progression of islet allograft rejection, but also the onset of GVHD.

Figure 12:
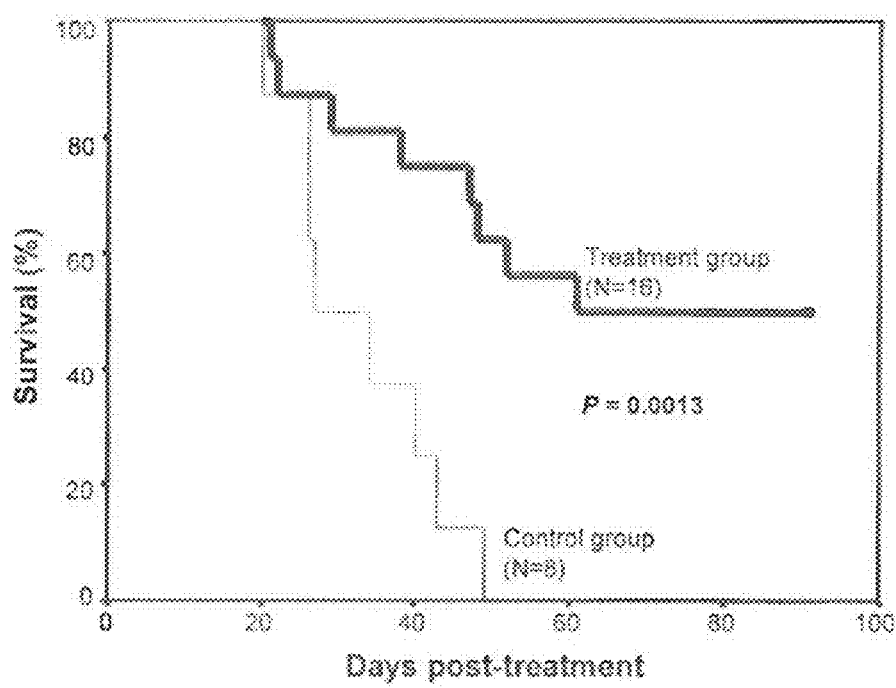

In addition, we found that even after excluding the IgG-treated mice that failed to maintain euglycemia, and comparing animals that remained euglycemic, host survival time was prolonged significantly in the group receiving ILT3-Fc compared to control IgG (FIG. 12). While all euglycemic mice in the IgG-treated control group (N=8) died within 7 weeks, 50% of ILT3-treated mice (8 out of 16) survived for more that 13 weeks (p<0.0013) (FIG. 12), demonstrating the effectiveness of ILT3-Fc in treating GVHD.

To further demonstrate the effectiveness of sILT3 in preventing the development of or treating GVHD, a similar study as above is conducted, without the induction of diabetes or islet cell transplantation. SCID mice are "humanized" by intraperitoneal (i.p.) injection of $50 \times 10^6$ freshly isolated human PBMC and assigned either to the treatment group, which receives a daily i.p. injection of sILT3 over a period of 10 days starting the day of PBMC injection, or to the control group which receives human IgG instead.

Host survival time is prolonged significantly in the group receiving ILT3-Fc compared to control IgG treatment. While many IgG-treated mice develop GVHD and die, a significantly larger fraction of ILT3-treated mice remain free of GVHD and survive through the course of the study period. The average survival time of the ILT3-Fc-treated group is significantly longer than that of the IgG-treated control group. Subsequent histological studies on the mice show no signs, less severe signs, or a delayed development of GVHD in mice from the ILT3-Fc-treated group compared to controls. Therefore, sILT3 is effective in treating, preventing, or delaying the development of GVHD.

EXAMPLE 8

ILT3-Fc Inhibits CD40 Signaling in Pancreatic Islet cells

Pancreatic islet β cells express the costimulatory CD40 molecule. Like in APCs, CD40 expression in β cells is upregulated by cytokines and CD40L, and signaling through CD40 activates NF-κB (Klein D, et al., 2005; Cardozo A K et al., 2001). We demonstrated that allospecific, ILT3-Fc-induced CD8+ $T_S$ cells are able to suppress the stimulation of CD40 expression in islet cells.

Responding T-cells were allostimulated with irradiated PBMC matching the HLA classes I and II of selected islet cultures in the presence of 50 μg/ml ILT3-Fc. After 7 days, CD8$^+$ T-cells were isolated and tested. Unprimed CD8$^+$ T-cells from the same responder served as controls. Pancreatic islets selected as targets were co-incubated overnight with one of the following: 1) CD40L-transfected (CD40L$^+$) D1.1 cells only; 2) CD40L+D1.1 cells plus allospecific CD8$^+$ $T_S$ cells; or 3) CD40L+D1.1 cells plus unprimed CD8$^+$ T-cells. The islet cells, CD8$^+$ T-cells, and the D1.1 cells were added at a 1:1:1 ratio. In addition, islets cultured alone were used to measure the constitutive level of CD40 expression, and islets cultured in tumor necrosis factor-α ($10^6$ units/l), IFN-γ ($10^6$ units/l), and interleukin (IL)-1β ($5 \times 10^4$ units/l) were used as a positive control for CD40 induction. After 18 h, cells were washed and the T-cells were depleted. The T-cell depletion was done by magnetic separation, i.e., incubating the cells with mouse anti-CD3 and anti-CD8 antibodies (Becton Dickinson, San Jose, Calif.), then incubating with by anti-mouse antibodies fused to magnetic beads (Invitrogen, Carlsbad, Calif.). The cells remaining after magnetic separation, enriched in human islet cells, were used for PCR and flow-cytometry studies.

Figure 16:
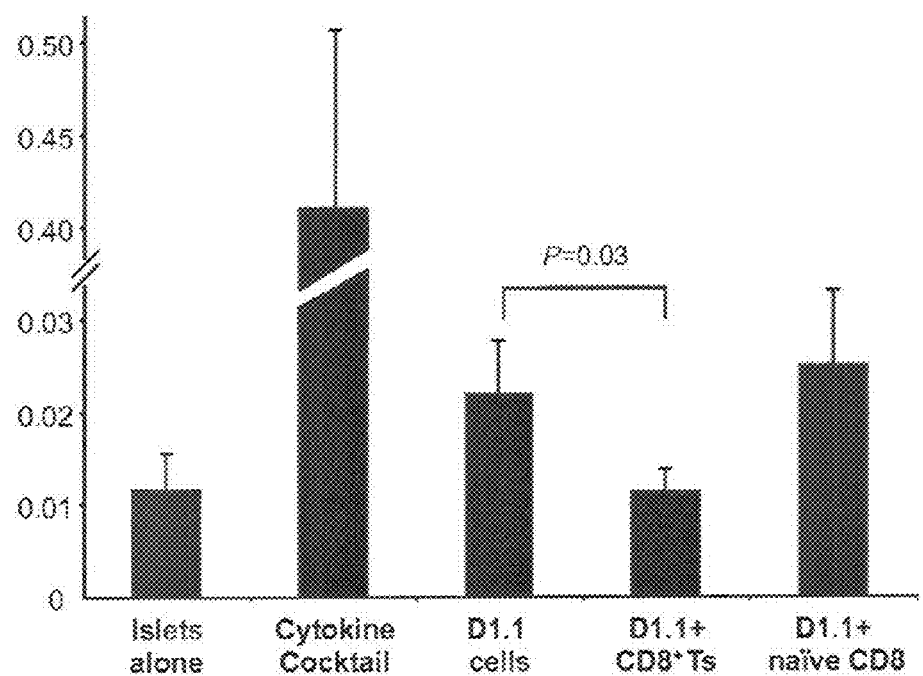
Figure 17:
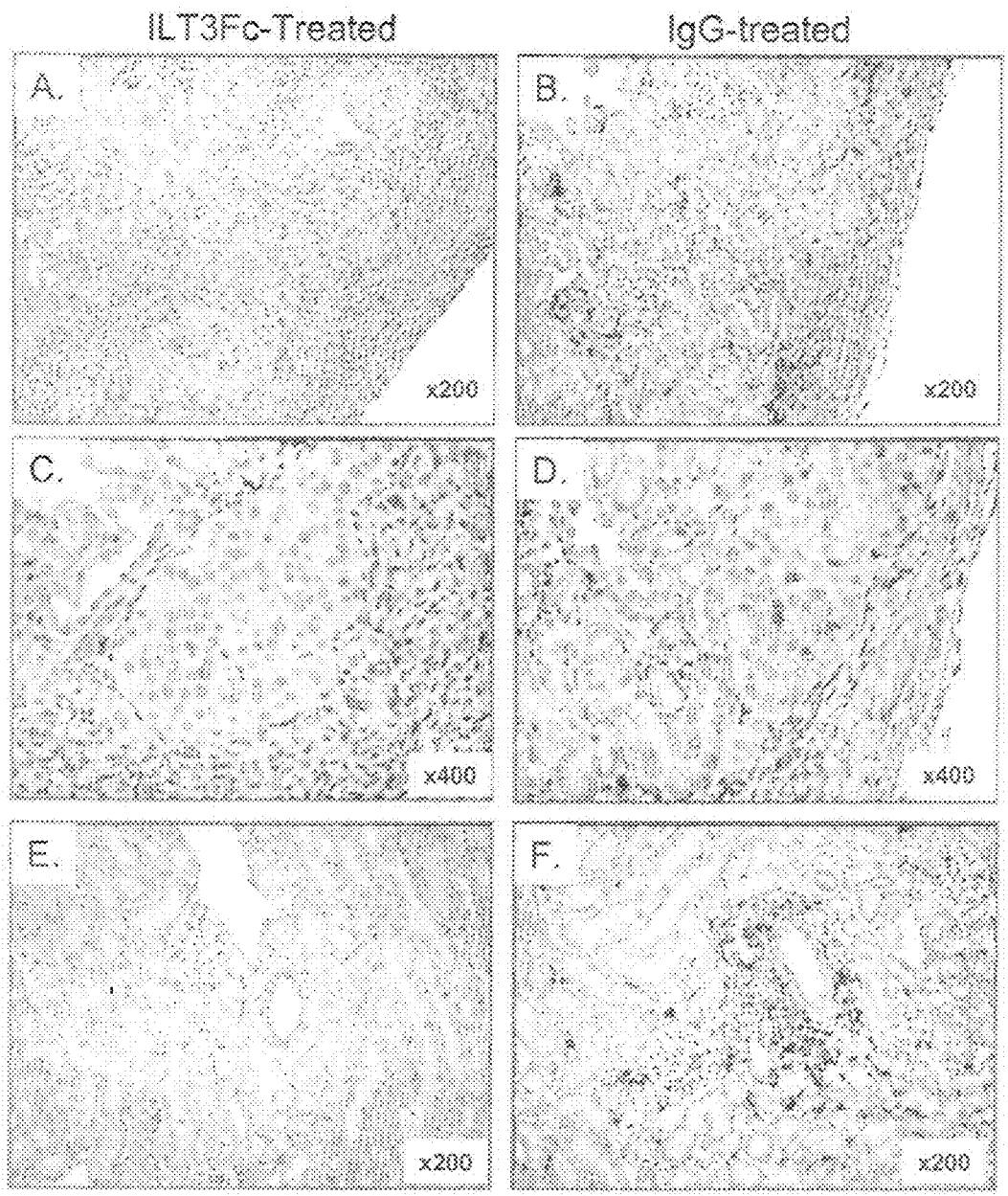

Real time PCR analysis of the isolated islet cells showed (see FIG. 16) that the cytokine mixture induced maximal upregulation of CD40 expression in pancreatic islets. CD40L$^+$ D1.1 cells induced the transcriptional upregulation of CD40, confirming that the presence of CD40L induces CD40 expression in these islet cells. The presence of primed CD8$^+$ T$_S$ cells inhibited the CD40L$^+$ D1.I-induced upregulation of CD40 to baseline levels (i.e. similar to CD40 expression levels in islets cultured alone). Unprimed CD8$^+$ T cells, however, had no effect on inhibiting CD40 expression in islet cells triggered by CD40L-expressing D1.1 cells. These results demonstrate that allospecific CD8$^+$ T$_S$ cells suppress CD40L-induced upregulation of CD40 in human pancreatic islet cells.

Prevention or Treatment of Autoimmune Destruction of Islet Cells by Administration of sILT3

Selective autoimmune destruction of native islet cells occurs spontaneously or in combination with islet graft rejection in diabetic patients even while they are receiving immuno-suppressive therapy, and the discovery of agents that block both of these pathologic processes would be useful.

The constitutive and selective expression of CD40 on the surface of β cells contribute to autoimmunity and islet allograft rejection by providing costimulatory signals to the infiltrating lymphocytes. The capacity of CD8$^+$ T$_S$ cells to inhibit CD40 signaling in pancreatic β cells is one mechanism underlying Ts-mediated suppression of transplant rejection. In addition, previous work has shown that spontaneous diabetes in NOD mice is inhibited by treatment with anti-CD40L antibodies (Balasa B et al., 1997) and such treatment also prolonged islet allograft survival in rodent transplantation models (Philips N E et al., 2003).

We demonstrate that the administration of ILT3-Fc treats diabetes that arises due to selective autoimmune destruction of native islet cells, by inhibiting the CD40-CD40L interaction between pancreatic islet cells (expressing CD40) and autoaggressive T cells (expressing CD40L) that have been primed to diabetogenic islet cell peptides presented by self-APC.

To demonstrate the effectiveness of sILT3 in preventing and/or treating autoimmune diabetes, 3-week-old Non-obese diabetic (NOD) mice are treated with either ILT3-Fc or IgG. NOD mice are known to spontaneously develop type 1, T cell-dependent autoimmune diabetes, starting from about 3-4 weeks postnatal, as a result of insulitis, a leukocytic infiltration of the pancreatic islets. The NOD mice treated with ILT3-Fc maintain euglycemia, and show no histological sign of insulitis, while control mice treated with IgG develop hyperglycemia and insulitis. Treatment of such mice with ILT3-Fc at >9 weeks of age inhibits and/or reverses the disease process. Euglycemia is restored upon treatment with ILT3-Fc, and subsequent histology on the mice shows little or no sign of insulitis. Therefore, sILT3 is effective in treating diabetes due to selective autoimmune destruction of native islet cells.

Cited Documents

Leukocyte Immunoglobulin-like Receptor, Subfamily B, Member 4; LILRB4. OMIM 604821 (2000).

Beinhauer B. G., et al. (2004) Interleukin 10 regulates cell surface and soluble LIR-2 (CD85d) expression on dendritic cells resulting in T cell hyporesponsiveness in vitro. Eur. J. Immunol. 34:74-80.

Colonna M., et al., U.S. Patent Publication No. 20030165875, published Sep. 4, 2003.

Balasa, B., et al. (1997) CD40 ligand-CD40 interactions are necessary for the initiation of insulitis and diabetes in non-obese diabetic mice. J. Immunol. 159:4620-4627.

Cardozo, A. K., et al. (2001) A comprehensive analysis of cytokine-induced and nuclear factor-kappa B-dependent genes in primary rat pancreatic beta-cells. J Biol Chem 276:48879-48886.

Davalli, A. M., et al. (1996) Vulnerability of islets in the immediate posttransplantation period: Dynamic changes in structure and function. Diabetes 45:1161-1167

Gregori, S., et al. (2005) An anti-CD45RO/RB monoclonal antibody modulates T cell responses via induction of apoptosis and generation of regulatory T cells. J. Exp. Med. 201:1293-1305.

Hoffmann-Fezer G., et al. (1993) Immunohistology and immunocytology of human T-cell chimerism and graft-versus-host disease in SCID mice. Blood. June 15; 81(12): 3440-3448.

Jiang, S. S., et al. (1998) Induction of MI-IC-class I restricted human suppressor T cells by peptide priming in vitro. Hum. Immunol. 59:690-699.

Klein, D., et al. (2005) A functional CD40 receptor is expressed in pancreatic beta cells. Diabetologia 48:268-276.

Phillips, N. E., et al. (2003) Blockade of CD40-mediated signaling is sufficient for inducing islet but not skin transplantation tolerance. J. Immunol. 170:3015-3023.

Vlad, G. R., et al. (2005) License to heal: bidirectional interaction of antigen-specific regulatory T cells and tolerogenic APC. J. Immunol. 174:5907-5914.

What is claimed is:

1. A method comprising
   1. identifying a subject having autoimmune diabetes in need of immune suppression, and
   2. administering to the subject an immunosuppressive amount of a soluble polypeptide comprising the extracellular domain of human ILT3.

2. The method of claim 1, wherein the polypeptide is administered subcutaneously, intradermally, intravenously, or intraperitoneally.

3. The method of claim 1, wherein the polypeptide further comprises a Fc portion of an immunoglobulin.

4. The method of claim 3, wherein the Fc portion of an immunoglobulin is an Fc portion of IgG1.

5. The method of claim 4, wherein the IgG1 is a human IgG1.

6. The method of claim 3, wherein the Fc portion further comprises a function-enhancing mutation that inhibits binding of the Fc portion to an Fc receptor.

7. The method of claim 6, wherein the function-enhancing mutation in the Fc portion comprises an Asn-->Gln point mutation at the N-linked glycosylation site.

8. The method of claim 1, wherein the subject is a mammal.

9. The method of claim 8, wherein the subject is a human.

10. The method of claim 1, further comprising administering to the subject an effective amount of another immunosuppressive agent.

* * * * *

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccatgatatc aggagacgcc atgatcccca                                    30
```

```
<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgtagcggc cgcgttttct ccctggacgt ca                              32
```